US011318479B2

(12) United States Patent
Chapman et al.

(10) Patent No.: US 11,318,479 B2
(45) Date of Patent: May 3, 2022

(54) CAPTURING SPECIFIC NUCLEIC ACID MATERIALS FROM INDIVIDUAL BIOLOGICAL CELLS IN A MICRO-FLUIDIC DEVICE

(71) Applicant: Berkeley Lights, Inc., Emeryville, CA (US)

(72) Inventors: Kevin T. Chapman, Santa Monica, CA (US); Eric D. Hobbs, Livermore, CA (US); Steven W. Short, Pleasanton, CA (US); Mark P. White, San Francisco, CA (US); Daniele Malleo, San Jose, CA (US)

(73) Assignee: Berkeley Lights, Inc., Emeryville, CA (US)

(*) Notice: Subject to any disclaimer, the term of this patent is extended or adjusted under 35 U.S.C. 154(b) by 974 days.

(21) Appl. No.: 15/105,849

(22) PCT Filed: Dec. 18, 2014

(86) PCT No.: PCT/US2014/071323

§ 371 (c)(1),
(2) Date: Dec. 6, 2016

(87) PCT Pub. No.: WO2015/095623

PCT Pub. Date: Jun. 25, 2015

(65) Prior Publication Data

US 2017/0021366 A1 Jan. 26, 2017

Related U.S. Application Data

(63) Continuation-in-part of application No. 14/133,361, filed on Dec. 18, 2013, now abandoned.

(51) Int. Cl.
*C12Q 1/68* (2018.01)
*B03C 5/00* (2006.01)
(Continued)

(52) U.S. Cl.
CPC .......... *B03C 5/005* (2013.01); *B01L 3/50273* (2013.01); *B01L 3/502761* (2013.01);
(Continued)

(58) Field of Classification Search
CPC ............ C12Q 2547/101; C12Q 1/6876; B01L 2200/0647; B01L 2300/0829;
(Continued)

(56) References Cited

U.S. PATENT DOCUMENTS 6,958,132 B2 10/2005 Chiou et al.
7,956,339 B2 6/2011 Ohta et al.
(Continued)

FOREIGN PATENT DOCUMENTS

EP 2647434 B1 5/2017
JP 2007003386 A 1/2007
(Continued)

OTHER PUBLICATIONS

Rumble et al. "SHrimp: accurate mapping of short color-space reads" PLOS Computational Biology, May 2009, 5(5)(e1000386): pp. 1-11 (Year: 2009).*
(Continued)

*Primary Examiner* — Betty J Forman
(74) *Attorney, Agent, or Firm* — Kenneth E. Horton; Barnes & Thornburg LLP

(57) ABSTRACT

Individual biological cells can be selected in a micro-fluidic device and moved into isolation pens in the device. The cells can then be lysed in the pens, releasing nucleic acid material, which can be captured by one or more capture objects in the pens. The capture objects with the captured nucleic acid material can then be removed from the pens. The capture objects can include unique identifiers, allowing each capture object to be correlated to the individual cell from which the nucleic acid material captured by the object originated.

28 Claims, 17 Drawing Sheets

(51) Int. Cl.
*B03C 5/02* (2006.01)
*B03C 11/00* (2006.01)
*B01L 3/00* (2006.01)

(52) U.S. Cl.
CPC .............. *B03C 5/026* (2013.01); *B03C 11/00* (2013.01); *B01L 2200/0668* (2013.01); *B01L 2200/14* (2013.01); *B01L 2400/0424* (2013.01); *B03C 2201/26* (2013.01)

(58) Field of Classification Search
CPC ......... B01L 3/50853; B01L 2200/0652; B01L 3/502761; B01L 2400/0424; B01L 3/50273; B01L 2200/068; C12N 15/10; B03C 5/028; B03C 5/026; B03C 5/005; C12M 47/06; G01N 27/305
See application file for complete search history.

(56) References Cited

U.S. PATENT DOCUMENTS

| | | | | |
|---|---|---|---|---|
| 2003/0175947 | A1 | 9/2003 | Liu et al. | |
| 2004/0197905 | A1 | 10/2004 | Hafeman | |
| 2005/0274612 | A1 | 12/2005 | Segawa et al. | |
| 2006/0226012 | A1 | 10/2006 | Kanagasabapathi et al. | |
| 2007/0242105 | A1 | 10/2007 | Srinivasan et al. | |
| 2007/0243634 | A1 | 10/2007 | Pamula et al. | |
| 2009/0075826 | A1* | 3/2009 | Chakrabarty | B01L 3/502761 506/6 |
| 2009/0098541 | A1 | 4/2009 | Southern et al. | |
| 2009/0170186 | A1* | 7/2009 | Wu | B01L 3/502761 435/286.1 |
| 2010/0021910 | A1 | 1/2010 | Cao et al. | |
| 2010/0068706 | A1 | 3/2010 | Pourahmadi et al. | |
| 2011/0053151 | A1 | 3/2011 | Hansen et al. | |
| 2011/0262906 | A1 | 10/2011 | Dimov et al. | |
| 2012/0009671 | A1 | 1/2012 | Hansen et al. | |
| 2012/0015347 | A1 | 1/2012 | Singhal et al. | |
| 2012/0015382 | A1 | 1/2012 | Weitz et al. | |
| 2012/0156675 | A1* | 6/2012 | Lueerssen | B01L 3/50853 435/6.11 |
| 2012/0325665 | A1 | 12/2012 | Chiou et al. | |
| 2013/0118905 | A1 | 5/2013 | Morimoto et al. | |
| 2013/0130232 | A1 | 5/2013 | Weibel et al. | |
| 2014/0154703 | A1 | 6/2014 | Skelley et al. | |
| 2015/0018226 | A1 | 1/2015 | Hansen et al. | |
| 2015/0141261 | A1* | 5/2015 | Hunicke-Smith | C12Q 1/6806 506/2 |
| 2015/0148264 | A1 | 5/2015 | Esfandyarpour et al. | |

FOREIGN PATENT DOCUMENTS

| | | | |
|---|---|---|---|
| TW | 201211242 | A | 3/2012 |
| WO | 0046595 | A1 | 8/2000 |
| WO | 2004040001 | A2 | 5/2004 |
| WO | 2005095963 | A2 | 10/2005 |
| WO | 2007092713 | A2 | 8/2007 |
| WO | 2012024658 | A | 2/2012 |
| WO | 2012162779 | A1 | 12/2012 |
| WO | 2013130714 | A1 | 9/2013 |
| WO | 2014036915 | A1 | 3/2014 |
| WO | 2014153651 | A1 | 11/2014 |

OTHER PUBLICATIONS

U.S. Appl. No. 61/660,370 (Year: 2012).*
Sasuga et al. "Single-cell chemical lysis method for analyses of intracellular molecules using an array of picoliter-sclae microwells" Anal. Chem. 2008, 80: 9141-9149. (Year: 2008).*
Jen et al. "Single cell chemical lysis on microfluidic chips with array of microwells" Sensor, 2012, 12: 347-358. (Year: 2012).*
Ramadan, Q. et al., Simultaneous Cell Lysis and Bead Trapping in a Continous Flow Microfluidic Device. Sensors and Actuators B, Jun. 6, 2005. vol. 113, No. 2, pp. 944-955. Abstract, Sections 2.1, 3.2.4, 4.3; Figs. 1b,6,7,10.
Valley J K et al.: "Optoelectronic Tweezers as a Tool for Parallel Single Cell Manipulation and Stimulation", IEEE Transactions on Biomedical Circuits and Systems, IEEE, US, vol. 3, No. 6, Dec. 1, 2009 (Dec. 1, 2009), pp. 424-431.
European Patent Office, Office Action, Application Serial No. 14872873.6, dated Jun. 5, 2020 (4 pages).
Lee et al., "Microchip-based one step DNA extraction and real-time PCR in one chamber for rapid pathogen identification" Lab on Chip 2006.
Nevill et al., Integrated microfluidic cell culture and lysis on a chip, Lab on a Chip 7:1689-95 (2007).
Z REPORT_The International Search Report and the Written Opinion of the International Searching Authority, PCT Application Serial No. PCT/US2014/071323 (dated Mar. 26, 2015), 12 pages.

* cited by examiner

1400

CAPTURING SPECIFIC NUCLEIC ACID MATERIALS FROM INDIVIDUAL BIOLOGICAL CELLS IN A MICRO-FLUIDIC DEVICE

BACKGROUND

In biological fields, it can be useful to extract and capture nucleic acid materials from biological cells. Examples of such nucleic acid materials include deoxyribonucleic acid (DNA), ribonucleic acid (RNA), polymers of DNA or RNA, organelles containing DNA or RNA, organelles containing polymers or oligomers of DNA or RNA, and the like. Embodiments of the present invention include devices and processes for extracting and selectively capturing specific types of nucleic acid materials from individual biological cells.

SUMMARY

In some embodiments of the invention, a process of capturing nucleic acid material from individual biological cells can include disposing individual biological cells into different isolation pens in a micro-fluidic device. The process can also include lysing one of the cells in the isolation pens and capturing with a capture object in the isolation pen nucleic acid material from the lysed cell. The process can further include removing the capture object from the isolation pen.

In some embodiments of the invention, a micro-fluidic device can include a common space, isolation pens, capture objects, and selecting means. The capture objects can be sized to be placed in one of the isolation pens. Each of the capture objects can comprise a capture material that binds to a particular type of nucleic acid material with at least two times greater specificity than it binds to other types of nucleic acid material. The selecting means can be for moving the selected individual cells into different isolation pens.

In some embodiments of the invention, a micro-fluidic device can include isolation pens, moving means, and correlation means. The isolation pens can be sized to contain a biological cell and a capture object, which can be configured to capture nucleic acid from the biological cell. The moving means can be for moving individual biological cells into the isolation pens. The correlation means can be for generating a correlation record correlating capture objects in the isolation pens with clonal cell colonies from which the biological cells in the isolation pens originated.

BRIEF DESCRIPTION OF THE DRAWINGS

FIG. 16A is an image of pens that contain cells prior to introduction of lysis buffer into the microfluidic device. FIGS. 16B, 16C, and 16D are images of the same pens at time t=0 minutes, 5 minutes, and 10 minutes, respectively, after introduction of the lysis buffer. Calcien AM staining of cells is used as a marker to monitor cell lysis.

DETAILED DESCRIPTION OF EXEMPLARY EMBODIMENTS

Figure 1:
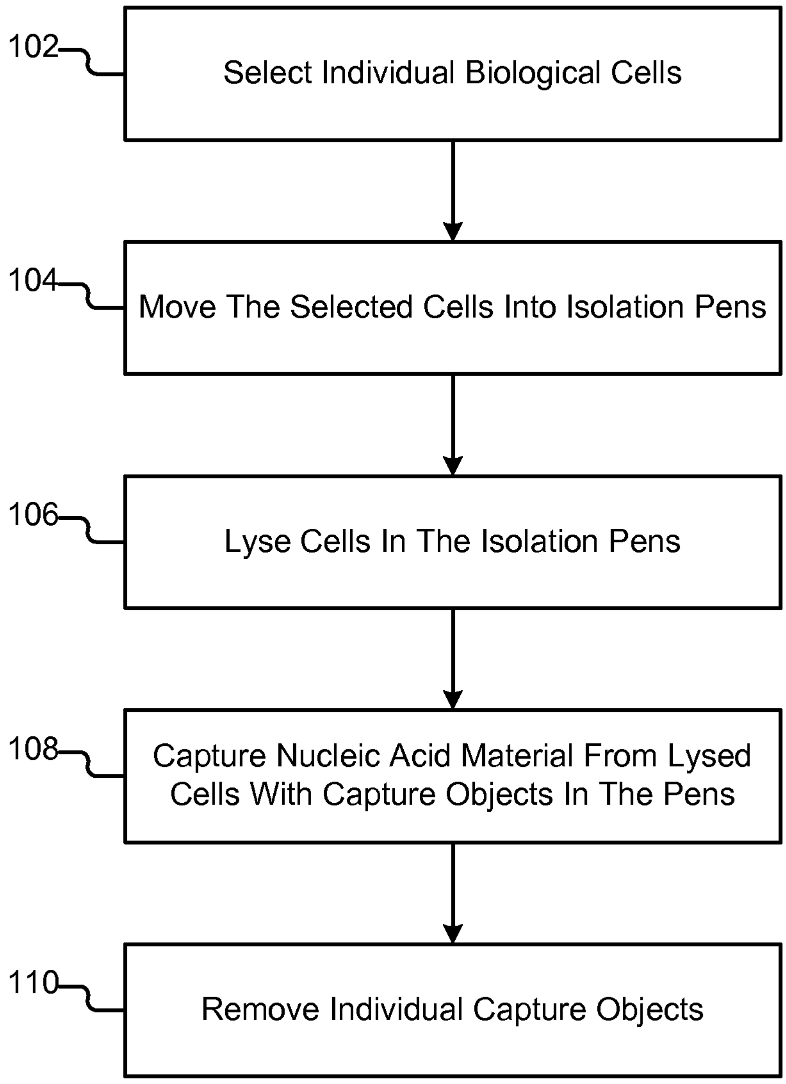
FIG. 1 is an example of a process for selectively capturing nucleic acid material from biological cells according to some embodiments of the invention.

This specification describes exemplary embodiments and applications of the invention. The invention, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms “on,” “attached to,” or “coupled to” are used herein, one element (e.g., a material, a layer, a substrate, etc.) can be “on,” “attached to,” or “coupled to” another element regardless of whether the one element is directly on, attached to, or coupled to the other element or there are one or more intervening elements between the one element and the other element. Also, directions (e.g., above, below, top, bottom, side, up, down, under, over, upper, lower, horizontal, vertical, “x,” “y,” “z,” etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements.

As used herein, “substantially” means sufficient to work for the intended purpose. The term “substantially” thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, “substantially” means within ten percent. The term “ones” means more than one.

As used herein, the term “disposed” encompasses within its meaning “located.”

As used herein, the term “capture object” can encompass one or more of the following: inanimate micro-objects such as microparticles, microbeads (e.g., polystyrene beads, Luminex™ beads, or the like), magnetic beads, microrods, microwires, quantum dots, and the like; biological micro-objects such as cells, liposomes (e.g, synthetic or derived from membrane preparations), lipid nanorafts, and the like; or a combination of inanimate micro-objects and biological micro-objects (e.g., microbeads attached to cells, liposome-coated micro-beads, liposome-coated magnetic beads, or the like). Lipid nanorafts have been described, e.g., in Ritchie et al. (2009) “Reconstitution of Membrane Proteins in Phospholipid Bilayer Nanodiscs,” Methods Enzymol., 464:211-231.

The term “cell” means a biological cell, which can be a plant cell, an animal cell, a bacterial cell, a fungal cell, embryos, oocytes, sperms, cells dissociated from a tissue, blood cells, hydridomas, cultured cells, cells from a cell line, cancer cells, infected cells, transfected and/or transformed cells, reporter cells, and the like. An animal cell can be, for example, from a mammal, such as a human, a mouse, a rat, a horse, a goat, a sheep, a cow, a primate, or the like.

As used with respect to a biological cell, “lyse” means to break, rupture, or otherwise compromise at least a membrane of the cell sufficiently to release nucleic acid material from the cell. When used with respect to a biological cell, “internal element” means any element or component of a biological cell that is inside the outer membrane of the cell and bounded by its own membrane, and lysing an internal element means breaking, rupturing, or otherwise compromising the membrane of the element sufficiently to release nucleic acid from the element. Examples of internal elements of a cell include a nucleus of the cell and organelles.

In some embodiments of the invention, individual biological cells can be selected in a micro-fluidic device based on any of a number of different possible characteristics. Nucleic acid material can then be extracted from an individual cell while the cell is in an isolation pen in the micro-fluidic device. Capture objects in the pen can each capture a specific type of the nucleic acid material from the cell, after which the capture objects can be removed from the pen and, for example, exported from the micro-fluidic device. The capture objects can include unique identifiers, allowing each capture object to be correlated to the individual cell from which the nucleic acid material captured by the object originated. The unique identifiers can also provide additional information such as the type of nucleic acid material captured from the cell.

FIG. 1 illustrates an example of a process 100 in which individual biological cells can be selected in a micro-fluidic device at step 102 and moved into isolation pens in the device at step 104. Alternatively, individual cells already in the pens can be selected for one or more particular characteristics at step 102, and the cells in the pens that lack that characteristic or characteristics can be moved out of the pens at step 104, leaving selected cells in the pens. Regardless, the selected cells can be lysed in the isolation pens at step 106, releasing nucleic acid material from the lysed cells into the pens. At step 108, capture objects in the pens can capture specific types of the nucleic acid material. The capture objects can then be removed from the pens at step 110 and exported from, stored in, or further processed in the micro-fluidic device.

Figure 2A:
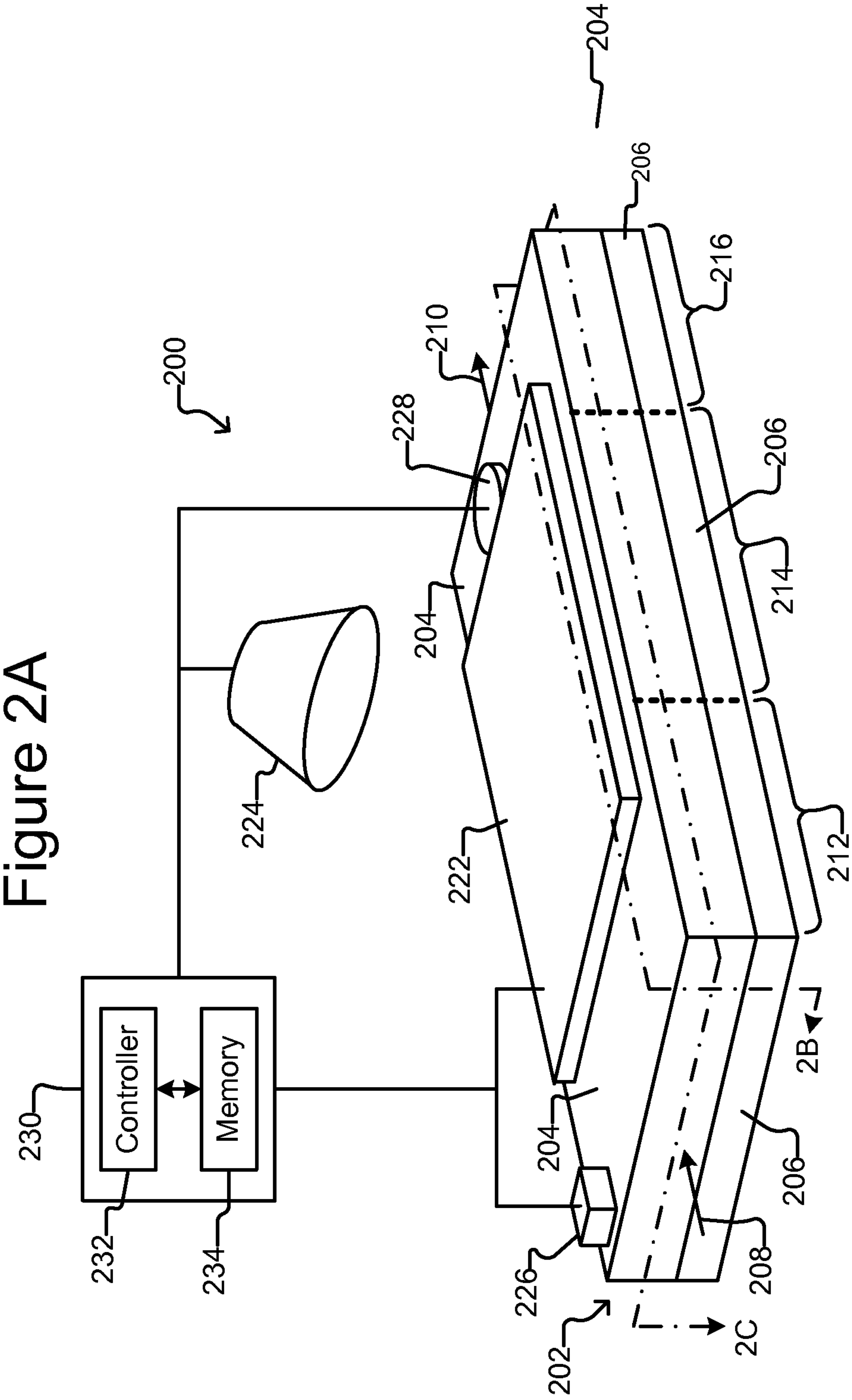
FIG. 2A is a perspective view of a micro-fluidic device with which the process of FIG. 1 can be performed according to some embodiments of the invention.
Figure 2B:
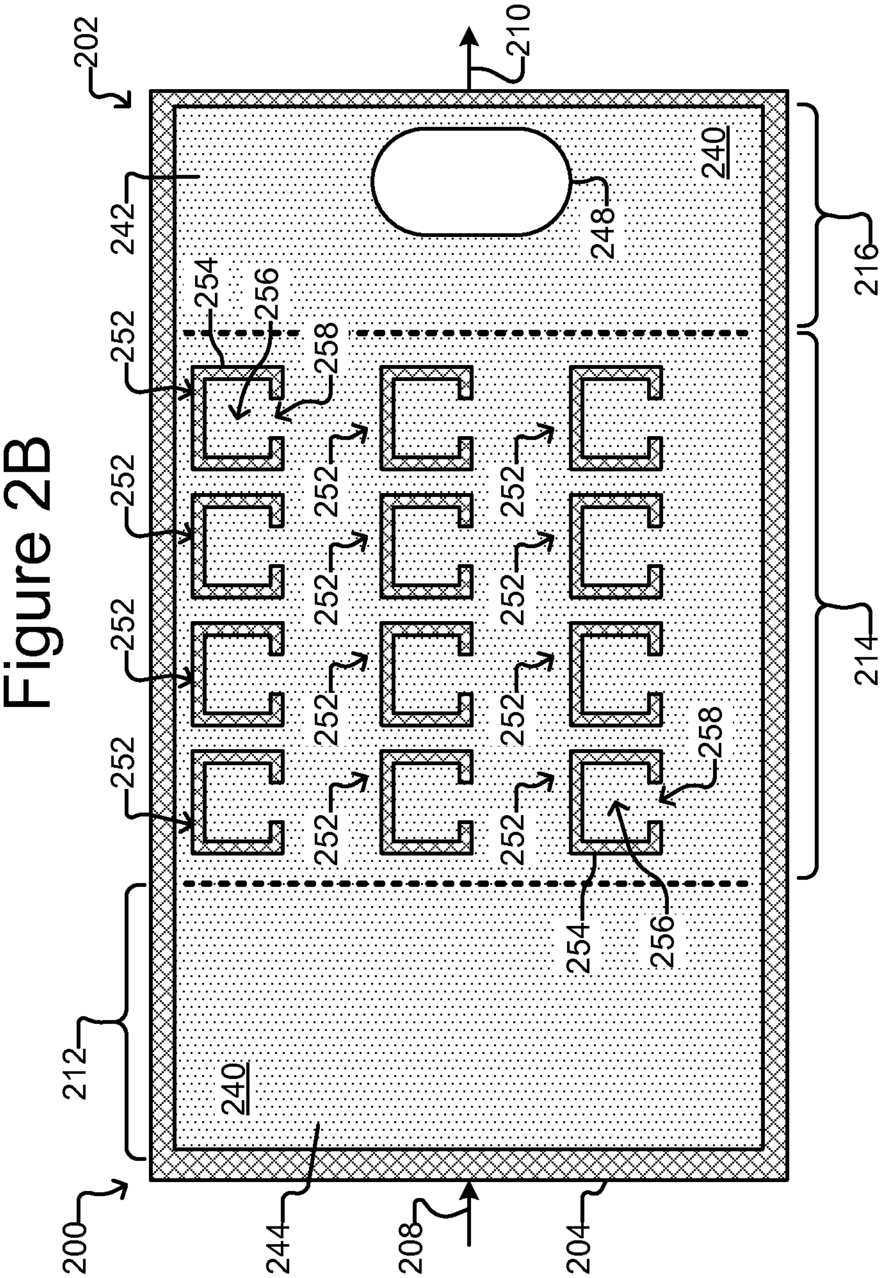
FIG. 2B is a top, cross-sectional view of the micro-fluidic device of FIG. 2A.
Figure 2C:
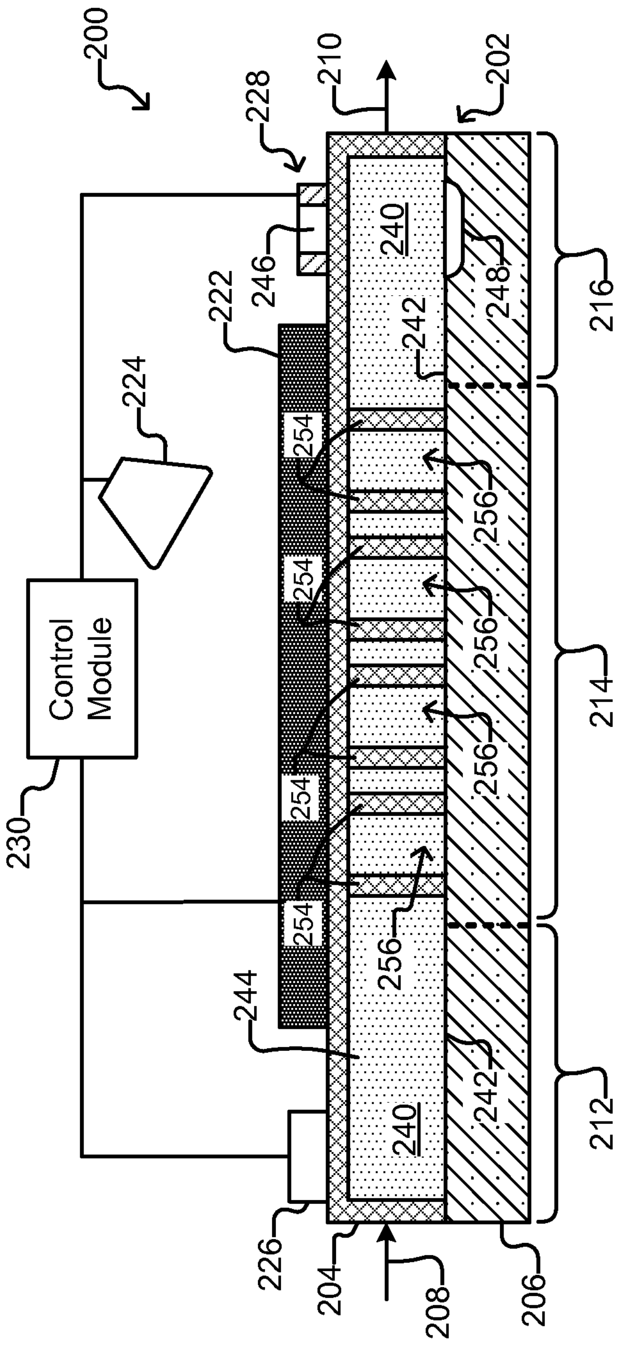
FIG. 2C is a side, cross-sectional view of the micro-fluidic device of FIG. 2A.
Figure 4A:
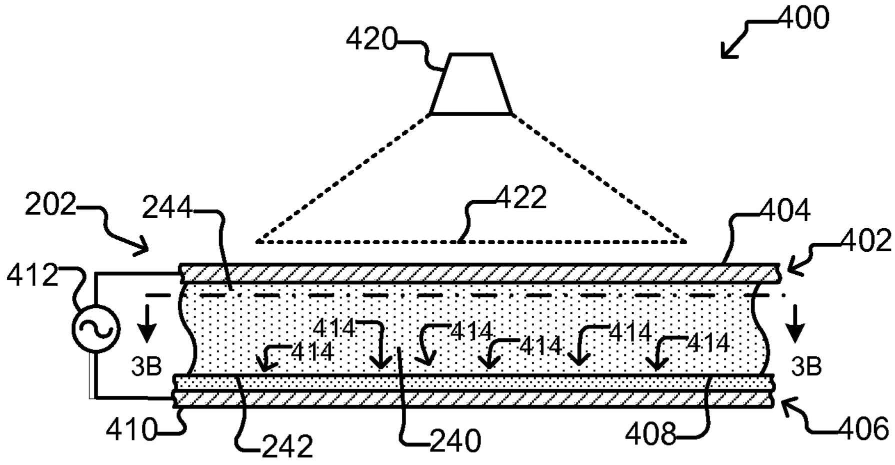
FIG. 4A is a partial side, cross-sectional view of the micro-fluidic device of FIGS. 2A-2C in which the manipulator is configured as an opto-electronic tweezer (OET) device according to some embodiments of the invention.
Figure 4B:
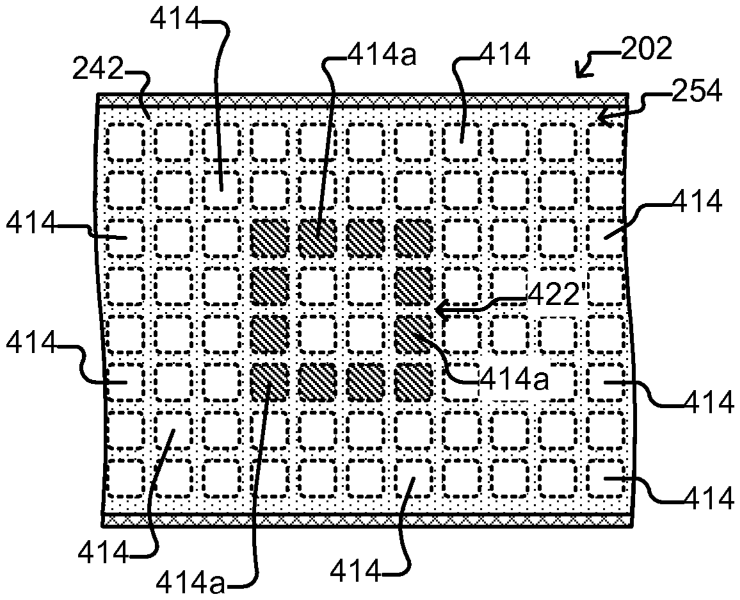
FIG. 4B is a partial top, cross-sectional view of FIG. 4A.

FIGS. 2A-2C show an example of a micro-fluidic device 200 on which the process 100 of FIG. 1 can be performed, and FIGS. 4A and 4B illustrate an example of the manipulator 222 of the device 200 configured as an opto-electronic tweezers (OET) device. FIGS. 5-12 illustrate an example of the process 100 of FIG. 1 performed on the micro-fluidic device 200 the manipulator 222 configured as an OET device, for example, as illustrated in FIGS. 4A and 4B. Before turning to the example of the process 100 performed with the device 200 illustrated in FIGS. 5-12, the micro-fluidic device 200 is discussed.

FIGS. 2A-2C illustrate an example of a micro-fluidic device 200 on which the process 100 can be performed. As shown, the micro-fluidic device 200 can comprise a housing 202, a manipulator 222, a detector 224, a flow controller 226, an export mechanism 228, and a control module 230.

As shown, the housing 202 can comprise one or more channels 240 for containing a liquid medium 244. FIG. 2B illustrates an inner surface 242 of the channel 240 on which the medium 244 can be disposed as even (e.g., flat) and featureless. The inner surface 242, however, can alternatively be uneven (e.g., not flat) and comprise features such as electric terminals (not shown).

The housing 202 can comprise one or more inlets 208 through which the medium 244 can be input into the channel 240. An inlet 208 can be, for example, an input port, an opening, a valve, another channel, fluidic connectors, or the like. The housing 202 can also comprise one or more outlets 210. For example, medium 244 can be removed through the outlet 210. An outlet 210 can be, for example, an output port, an opening, a valve, another channel, fluidic connectors, or the like. As another example, an outlet 210 can comprise a droplet outputting mechanism such as any of the outputting mechanisms disclosed in U.S. patent application Ser. No. 13/856,781 filed Apr. 4, 2013. All or part of the housing 202 can be gas permeable to allow gas (e.g., ambient air) to enter and exit the channel 240.

Although one inlet 208 and one outlet 210 are illustrated, there can be more than one inlet 208 and/or more than one outlet 210. Moreover, the inlets 208 and/or outlets 210 can be in different locations than shown in FIGS. 2A-2C. For example, there can be an outlet (not shown) from what will be described below as the selection portion 212 of the device 200 for waste such as unselected cells.

The housing 202 can also comprise a micro-fluidic structure 204 disposed on a base (e.g., a substrate) 206. The micro-fluidic structure 204 can comprise a flexible material (e.g. rubber, plastic, an elastomer, silicone, polydimethylsiloxane ("PDMS"), or the like), which can be gas permeable. Alternatively, the micro-fluidic structure 204 can comprise other materials including rigid materials, or combinations of flexible and rigid materials. Examples of micro-fluidic structures that define microfluidic elements, such as channels and chambers (or pens), which are bounded at least in part by flexible (e.g., deformable) surfaces are described in U.S. Provisional Patent Application 62/089,065 (filed Dec. 8, 2014), the entire contents of which are incorporated herein by reference. The base 206 can comprise one or more substrates. Although illustrated as a single structure, the base 206 can comprise multiple interconnected structures such as multiple substrates. The micro-fluidic structure 204 can similarly comprise multiple interconnected structures.

The micro-fluidic structure 204 and the base 206 can define a channel 240, and/or one or more chambers (e.g., isolation pens 252). Although one channel 240 is shown in FIGS. 2A-2C, the micro-fluidic structure 204 and the base 206 can define multiple such channels, chambers, and/or the like for the medium 244, and such channels and chambers can be interconnect to form micro-fluidic circuits.

As shown in FIGS. 2B and 2C, isolation pens 252 can be disposed in the channel 240. For example, each isolation pen 252 can comprise an enclosure 254 that defines an interior space 256 and an opening 258 from the channel 240 to the interior space 256. There can be many such isolation pens 252 in the channel 240 disposed in any pattern, the isolation pens 252 can be any of many different sizes and shapes, and the pens 252 can have more than one opening 258. The opening 258 of each isolation pen 252 can be sized and positioned to allow for the natural exchange of liquid medium 244 in a pen 252 and liquid medium 244 flowing past the opening 258 of the pen 252 by, for example, diffusion. Alternatively, the opening 258 of each isolation pen 252 can be sized and positioned to allow droplets of aqueous medium (e.g., containing one or more cells, one or more capture objects, and/or reagents, such as lysis buffer) to be moved into or out of the isolation pens 252. Otherwise, however, the enclosures 254 can sufficiently enclose the interior spaces 256 of the pens 252 to prevent biological material or objects (not shown) (e.g., biological cells, secreted material, nucleic acid material, or the like) in the interior space 256 of one pen 252 from mixing with such biological material or objects in the interior space 256 of any another pen 252, and as will be described, prevent mixing of capture objects in one pen 256 from mixing with capture objects of another pen 256.

Although twelve pens 252 disposed in three rows are shown, there can be more or fewer pens 252, and the pens 252 can be disposed in other patterns. Moreover, the pens 252 can have different shapes, sizes, orientations, or the like than shown. For example, the pens 252 can have any of the shapes, sizes, or orientations or be disposed in any of the patterns disclosed in US2014/0116881 (filed Oct. 22, 2013) or U.S. patent application Ser. No. 14/520,568 (filed Oct. 22, 2014), the entire contents of which are incorporated herein by reference.

Isolation pens 252 comprising enclosures 254 that, as illustrated in FIG. 2C, extend the entire height of the channel 240 (e.g., from the surface 242 of the base 206 to the top of the micro-fluidic structure 204) are but an example and variations are contemplated. For example, the enclosures 254 need not extend the entire height of the channel 240.

Figure 3:
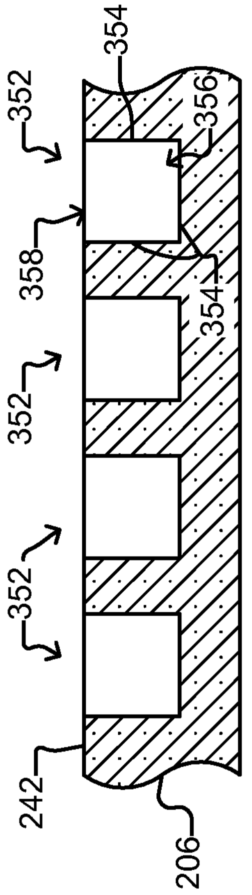
FIG. 3 is a partial, side cross-sectional view of the base of the micro-fluidic device of FIG. 2A illustrating examples of isolation pens configured as cavities into the base according to some embodiments of the invention.

FIG. 3 illustrates another example in which isolation pens 352 comprise cavities in the base 206 rather than enclosures 254. For example, as shown, each pen 352 can comprise an interior space 356 defined by sidewalls 354 of a cavity into the base 206. The opening 358 of each such pen 352 can be at the surface 242 of the base 206. Herein, any mention, discussion, illustration, or the like of a pen 252 can be replaced with a pen 352 in which the sidewalls 354, the interior space 356, and the opening 358 can correspond, respectively, to the enclosure 254, interior space 256, and opening 258 of a pen 252.

Figure 7:
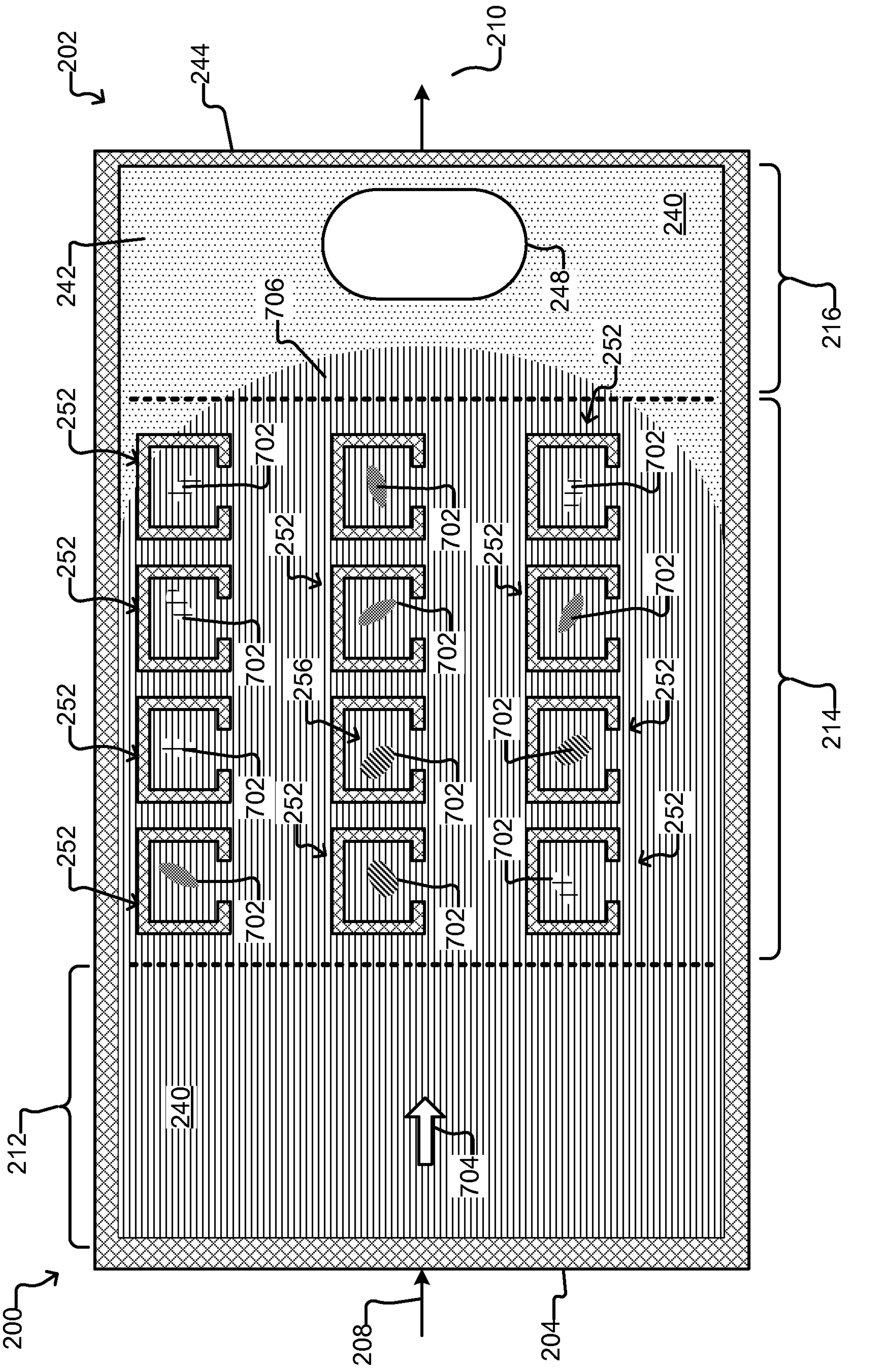
FIG. 7 shows an example of lysing cells in the isolation pens of the micro-fluidic device of FIGS. 2A-2C with a lysing reagent according to some embodiments of the invention.

Medium 244 can be flowed (e.g., from the inlet 208 to the outlet 210) past the openings 258 in the isolation pens 252. Such a flow of medium 244 can, for example, provide nutrients to biological objects (not shown) in the isolation pens 252. As another example, the flow of medium 244 can also provide for the removal of waste from the isolation pens 252. As will also be seen, the flow of medium 244 can cause material in the medium (e.g., a lysing reagent 706 as illustrated in FIG. 7, which is discussed below), to mix with medium 244 in the pens 252. Alternatively, the medium 244 can be an oil-based medium that contains droplets of aqueous medium. The droplets can contain cells, capture objects, and/or reagents (e.g., lysis buffer) that can be moved into the isolation pens 252, and optionally combined therein.

The manipulator 222 can be configured to create selectively electrokinetic forces on objects (not shown) in the medium 244. For example, the manipulator 222 can be configured to selectively activate (e.g., turn on) and deactivate (e.g., turn off) dielectrophoresis (DEP) electrodes at the inner surface 242 of the channel 240. The DEP electrodes can be each connected to an electrical connection through which current and/or voltage levels can be changed to individually activate and deactivate each electrode. As another example, the DEP electrodes can be light activated and deactivated such as in the example illustrated in FIGS. 4A and 4B and discussed below. Regardless, the DEP electrodes can create forces in the medium 244 that attract or repel objects (not shown) in the medium 244, and the manipulator 222 can thus select and move one or more objects in the medium 244.

For example, the manipulator 222 can comprise one or more optical (e.g., laser) tweezers devices, one or more optoelectronic tweezers (OET) devices (e.g., as disclosed in U.S. Pat. No. 7,612,355 (which is incorporated in its entirety by reference herein) or US2014/0124370, filed Oct. 10, 2013 (which is also incorporated in its entirety by reference herein)), and/or one or more devices having phototransistors (e.g., lateral bipolar transistors). As yet another example, the manipulator 222 can include one or more devices (not shown) for moving a droplet of the medium 244 in which one or more of objects are suspended. Such devices (not shown) can include electrowetting devices such as optoelectronic wetting (OEW) devices (e.g., as disclosed in U.S. Pat. No. 6,958,132, the entire contents of which are incorporated herein by reference), single-sided OEW devices (e.g., as disclosed in US2012/0024708, filed Jul. 31, 2011, or U.S. Provisional Application No. 62/088,532, filed Dec. 5, 2014, both of which are incorporated herein by reference in their entirety), or other electrowetting devices. The manipulator 222 can thus be characterized as a DEP device in some embodiments.

FIGS. 4A and 4B illustrate an example in which the manipulator 222 comprises an OET device 400, which is a type of DEP device. As shown, the OET device 400 can comprise a first electrode 404, a second electrode 410, an electrode activation substrate 408, a power source 412 (e.g., an alternating current (AC) power source), and a light source 420. Medium 244 in the channel 240 and the electrode activation substrate 408 can separate the electrodes 404, 410. Changing patterns of light 422 from the light source 420 can selectively activate and deactivate changing patterns of DEP electrodes at regions 414 of the inner surface 242 of the channel 240. (Hereinafter the regions 414 are referred to as "electrode regions.")

In the example illustrated in FIG. 4B, a light pattern 422' directed onto the inner surface 242 of the base 206 illuminates the cross-hatched electrode regions 414*a* in the square pattern shown. The other electrode regions 414 are not illuminated and are hereinafter referred to as "dark" electrode regions 414. The electrical impedance across the electrode activation substrate 408 from each dark electrode region 414 to the second electrode 410 is greater than the impedance from the first electrode 404 across the medium 244 in the channel 240 to the dark electrode region 414. Illuminating an electrode region 414*a*, however, reduces the impedance across the electrode activation substrate 408 from the illuminated electrode region 414*a* to the second electrode 410 to less than the impedance from the first electrode 404 across the medium 244 in the channel 240 to the illuminated electrode region 414*a*.

With the power source 412 activated, the foregoing creates an electric field gradient in the medium 244 between illuminated electrode regions 414*a* and adjacent dark electrode regions 414, which in turn creates local DEP forces that attract or repel nearby objects (not shown) in the medium 244. DEP electrodes that attract or repel objects in the medium 244 can thus be selectively activated and deactivated at many different such electrode regions 414 at the inner surface 242 of the channel 240 by changing light patterns 422 projected form a light source 420 (e.g., a laser source, a high intensity discharge lamp, or other type of light source) into the micro-fluidic device 200. Whether the DEP forces attract or repel nearby objects can depend on such parameters as the frequency of the power source 412 and the dielectric properties of the medium 244 and/or the objects (not shown).

The square pattern 422' of illuminated electrode regions 414*a* illustrated in FIG. 4B is an example only. Any pattern of the electrode regions 414 can be illuminated by the pattern of light 422 projected into the device 200, and the pattern of illuminated electrode regions 422' can be repeatedly changed by changing the light pattern 422.

In some embodiments, the electrode activation substrate 408 can be a photoconductive material, and the inner surface 242 can be featureless. In such embodiments, the DEP electrodes 414 can be created anywhere and in any pattern on the inner surface 242 of the channel 240 in accordance with the light pattern 422 (see FIG. 4A). The number and pattern of the electrode regions 414 are thus not fixed but correspond to the light pattern 422. Examples are illustrated in the aforementioned U.S. Pat. No. 7,612,355 in which the un-doped amorphous silicon material 24 shown in the drawings of the foregoing patent can be an example of photoconductive material that can compose the electrode activation substrate 408.

In other embodiments, the electrode activation substrate 408 can comprise a circuit substrate such as a semiconductor material comprising a plurality of doped layers, electrically insulating layers, and electrically conductive layers that form semiconductor integrated circuits such as is known in semiconductor fields. In such embodiments, electric circuit elements can form electrical connections between the electrode regions 414 at the inner surface 242 of the channel 240 and the second electrode 410 that can be selectively activated and deactivated by the light pattern 422. Non-limiting examples of such configurations of the electrode activation substrate 408 include the phototransistor-based OET device 400 illustrated in FIGS. 21 and 22 of U.S. Pat. No. 7,956,339 and the OET devices illustrated throughout the drawings in the aforementioned U.S. patent application Ser. No. 14/051,004. The phototransistors can be, for example, lateral bipolar phototransistors.

In some embodiments, the first electrode 404 can be part of a first wall 402 of the housing 202, and the electrode activation substrate 408 and second electrode 410 can be part of a second wall 406 of the housing 202 generally as illustrated in FIG. 4A. As shown, the channel 240 can be between the first wall 402 and the second wall 406. The foregoing, however, is but an example. In other embodiments, the first electrode 404 can be part of the second wall 406 and one or both of the electrode activation substrate 408 and/or the second electrode 410 can be part of the first wall 402. As another example, the first electrode 404 can be part of the same wall 402 or 406 as the electrode activation substrate 408 and the second electrode 410. For example, the electrode activation substrate 408 can comprise the first electrode 404 and/or the second electrode 410. Moreover, the light source 420 can alternatively be located below the housing 202.

Figure 6:
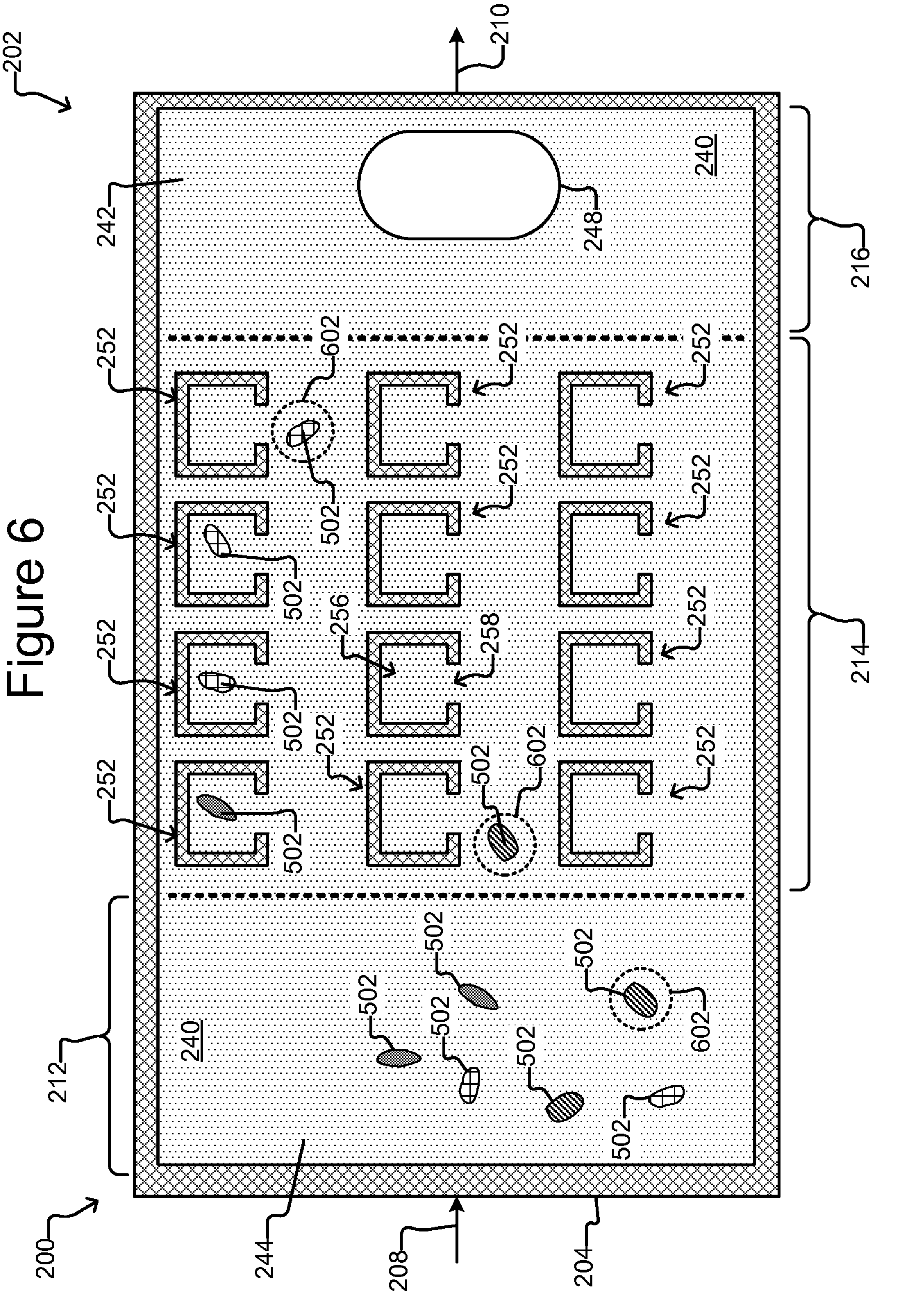
FIG. 6 is an example of selecting individual biological cells in the selection portion of the micro-fluidic device of FIGS. 2A-2C and moving the selected cells into isolation pens in the device according to some embodiments of the invention.

Configured as the OET device 400 of FIGS. 4A and 4B, the manipulator 222 can thus select an object (not shown) in the medium 244 in the channel 240 by projecting a light pattern 422 into the device 200 to activate one or more DEP electrodes at electrode regions 414 of the inner surface 242 of the channel 240 in a pattern that captures the object. The manipulator 222 can then move the captured object by moving the light pattern 422 relative to the device 200. Alternatively, the device 200 can be moved relative to the light pattern 422. Examples are illustrated in FIGS. 6 and 12 and discussed below. Although the enclosures 254 that define the isolation pens 252 are illustrated in FIGS. 2B and 2C and discussed above as physical enclosures, the enclosures 254 can alternatively be virtual enclosures comprising DEP forces activated by the light pattern 422.

As mentioned, the OET device 400 of FIGS. 4A and 4B is but an example of the manipulator 222. For example, although the electrode regions 414 are illustrated and discussed above as being activated and deactivated by a changing light pattern 422, device 400 can instead provide electrical connections (not shown) to each electrode region 414 (which can comprise an electrically conductive terminal at the surface 242) and individually activate and deactivate each electrode region 414 by controlling the voltage and/or current provided to each electrode region 414 through the electrical connections. So configured, the device 400 need not include the light source 420 or direct the light pattern 422 into the device 400. Another alternative is an OEW device, such as a single-sided OEW device, or a combined OET/OEW device, such as described in U.S. application Ser.

No. 14/262,140, filed Apr. 25, 2014, or U.S. application Ser. No. 14/262,200, filed Apr. 25, 2014, both of which are incorporated herein by reference in their entirety. In addition, forces that can be applied uniformly across a micro-fluidic device, such as gravity, can be used in conjunction with any of the foregoing, as described in U.S. Provisional Application No. 62/090,303, filed Dec. 10, 2014, the entire contents of which are incorporated herein by reference.

With reference again to FIGS. 2A-2C, it is noted that the detector 224 can be a mechanism for detecting events in the channel 240. For example, the detector 224 can comprise a photodetector capable of detecting one or more radiation characteristics (e.g., due to fluorescence or luminescence) of an object (not shown) in the medium. Such a detector 224 can be configured to detect, for example, that one or more objects (not shown) in the medium 244 are radiating electromagnetic radiation and/or the approximate wavelength, brightness, intensity, or the like of the radiation. Examples of suitable photodetectors include without limitation photo-multiplier tube detectors and avalanche photodetectors.

The detector 224 can alternatively or in addition comprise an imaging device for capturing digital images of the channel 240 including objects (not shown) in the medium 244. Examples of suitable imaging devices that the detector 224 can comprise include digital cameras or photosensors such as charge coupled devices and complementary metal-oxide-semiconductor imagers. Images can be captured with such devices and analyzed (e.g., by the control module 230). Such images can also be displayed on a display device such as a computer monitor (not shown).

The flow controller 226 can be configured to control a flow of the medium 244 in the channel 240. For example, the flow controller 226 can control the direction and/or velocity of the flow. Non-limiting examples of the flow controller 226 include one or more pumps or fluid actuators. In some embodiments, the flow controller 226 can include additional elements such as one or more sensors (not shown) for sensing, for example, the velocity of the flow of the medium 244 in the channel 240.

The export mechanism 228 can facilitate export of objects (not shown) from the micro-fluidic device 200. For example, as illustrated in FIGS. 2B and 2C, the export mechanism 228 can comprise a staging area 248 and a passage 246 through the housing 202. The passage 246 can alternatively be through the base 206 or a sidewall of the micro-fluidic structure 204. Objects (not shown) can be moved to the staging area 248 and exported from the device 200 through the passage 246. The export mechanism 228 can be, for example, like any of the examples of export mechanisms disclosed in U.S. patent application Ser. No. 14/520,510 (filed Oct. 22, 2014). Alternatively, the export mechanism 228 can simply comprise an outlet 210.

The control module 230 can be configured to receive signals from and control the manipulator 222, the detector 224, the flow controller 226, and/or the export mechanism 228. As shown, the control module 230 can comprise a controller 232 and a memory 234. In some embodiments, the controller 232 can be a digital electronic controller (e.g., a microprocessor, microcontroller, computer, or the like) configured to operate in accordance with machine readable instructions (e.g., software, firmware, microcode, or the like) stored as non-transitory signals in the memory 234, which can be a digital electronic, optical, or magnetic memory device. Alternatively, the controller 232 can comprise hard-wired digital circuitry and/or analog circuitry or a combination of a digital electronic controller operating in accordance with machine readable instructions and hardwired digital circuitry and/or analog circuitry.

As illustrated, the micro-fluidic device 200 can comprise a selection portion 212 (which can be an example of a common space in the device 200), an isolation portion 214, and/or an export portion 216. These portions 212, 214, 216 can be represent physical partitions of the device 200 or merely conceptual partitions. Regardless, as will be seen, biological cells (not shown) can be loaded into the selection portion 212, where individual ones of the biological cells (not shown) can be identified and selected. The isolation portion 214 can comprise the isolation pens 252, where the individual biological cells (not shown) selected in the selection portion 212 can be placed and isolated one from another.

As noted, FIGS. 5-12 illustrate an example of operation of the process 100 on the micro-fluidic device 200 of FIGS. 2A-2C. The process 100 is now discussed with reference to examples illustrated in FIGS. 5-12.

Figure 5:
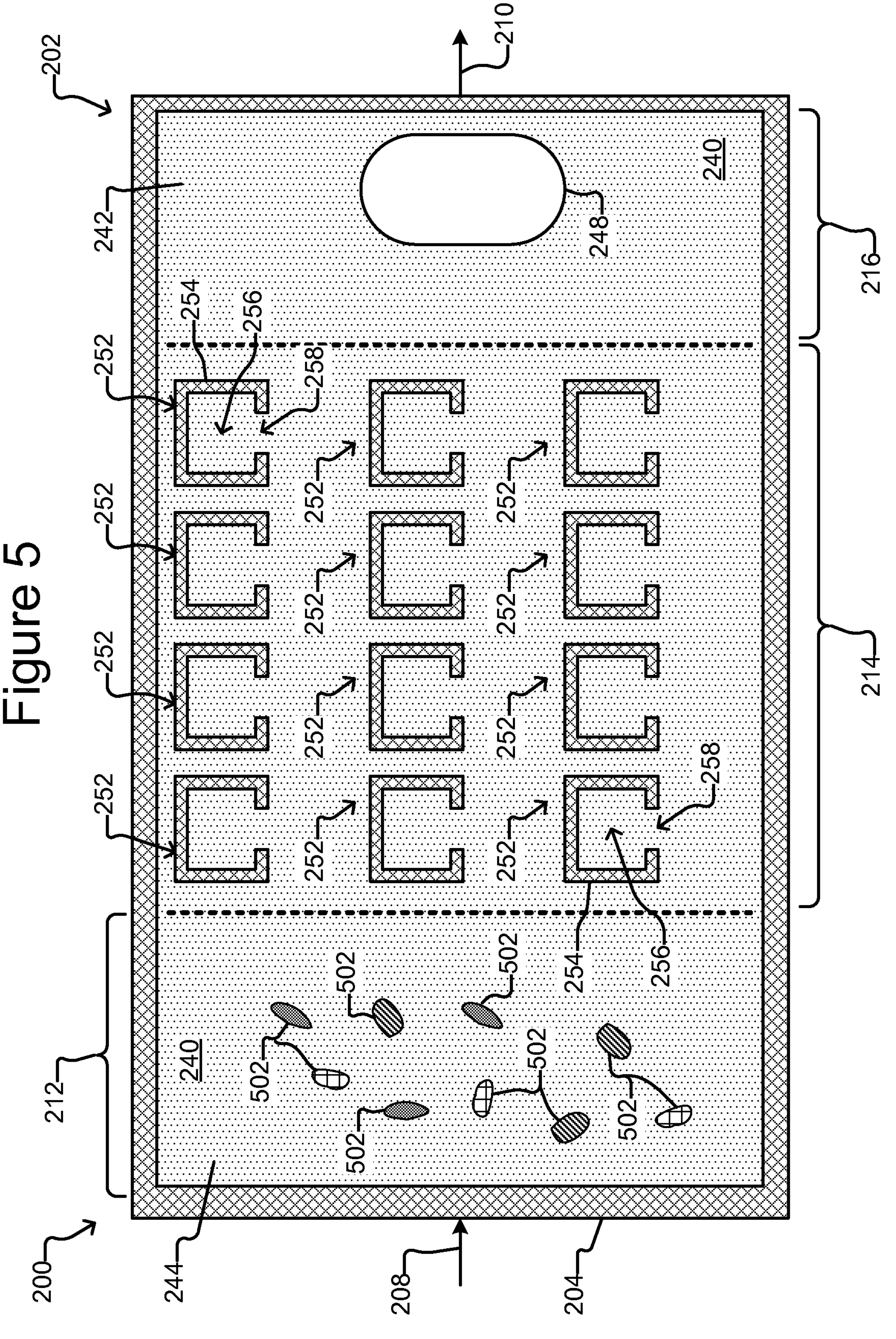
FIG. 5 illustrates an example of a plurality of cells in a selection portion of the micro-fluidic device of FIGS. 2A-2C according to some embodiments of the invention.

As shown in FIG. 1, at step 102, the process 100 can select individual biological cells. FIGS. 5 and 6 illustrate an example. As shown in FIG. 5, there can be biological cells 502 in the selection portion 212 of the micro-fluidic device 200. The cells 502 can all be the same type of cell. Alternatively, the cells 502 can comprise a variety of different types of cells. Regardless, the cells 502 can be loaded into the micro-fluidic device 200 through, for example, an inlet 208.

The process 100 can select one or more of the cells 502 individually based on any of a variety of different criteria or desired characteristics. For example, the process 100 can, as part of step 102, test the cells 502 in the selection portion 212 of the device 200 for one or more particular characteristics and select ones of the cells 502 determined to have the characteristic or characteristics. As another example, the process 100 can select ones of the cells 502 determined not to have the characteristic or characteristics.

Examples of characteristics that can be tested for as part of step 102 include the size and/or morphology (e.g., form and structure) of the cells 502. Thus, for example, the detector 224 can capture images of the cells 502 in the selection portion 212 of the device 200. The captured images of the cells 502 can then be analyzed to identify ones of the cells 502 that meet one or more predetermined size or morphology characteristics. For example, the captured images of the cells 502 can be analyzed to identify ones of the cells 502 that meet one or more of the following characteristics related to size: larger than, smaller than, or substantially equal to a predetermined threshold size or within a range of sizes between a high threshold size and a low threshold size. As another example, the captured images of the cells 502 can be analyzed to identify ones of the cells 502 that meet one or more predetermined morphology characteristics relating to the form and/or structure of the cells 502. Regardless, the captured images of the cells 502 can be displayed (e.g., on an electronic display device (not shown)) and analyzed by a human operator. Alternatively or in addition, the captured images of the cells 502 can be analyzed by the control module 230. For example, the control module 230 can comprise machine readable instructions (e.g., software, firmware, microcode, or the like) stored in the memory 234 and/or hardwired electrical circuits (not shown) for analyzing such images and identifying ones of the cells 502 that meet particular criteria regarding size or morphology.

Other examples of characteristics that can be tested for as part of step 102 include determining whether the cells 502 comprise or produce (e.g., express or secrete) one or more particular substances (e.g., a particular protein, a particular antibody, or the like). For example, the cells 502 can be treated (before or after being loaded into the selection portion 212 of the device 200) with a reagent that reacts in a distinct, detectable manner to the presence of one or more of such particular substances. Examples of such reagents include markers that stain cells 502 that comprise or produce a particular substance. The detector 224 can capture images of the treated cells 502 in the selection portion 212 of the device 200, and the images of the cells 502 can be analyzed to identify ones of the cells 502 that indicate the presence (or absence) of the particular substance. As noted, the images of the cells 502 can be displayed for and analyzed by a human user and/or analyzed by the control module 230 generally as discussed above. Methods of detecting cellular characteristics, such as size, morphology, and/or protein expression (e.g., antibody expression) have been described, for example, in U.S. application Ser. Nos. 14/520,568 and 14/521,447, both filed Oct. 22, 2014, and both of which are incorporated herein by reference in their entirety.

The detector 224 and/or the controller 230 programmed to analyze images of the cells 502 in the selection portion 212 of the device 200 can be an example of a means for identifying individual biological cells for a particular characteristic.

Thus, at step 102, the process 100 can test the cells 502 in the selection portion 212 of the device 200 for one or more specific characteristics (which can be different characteristics) and select one or more of the cells 502 that test positive for one or more of those specific characteristics. Alternatively, the process 100 can, at step 102, select one or more of the cells 502 that test negative for such characteristics.

Regardless, at step 104, the process 100 can move cells 502 selected at step 102 from the selection portion 212 of the device 200 into isolation pens 252 in the isolation portion 214 of the device 200. For example, each selected cell 502 can be moved into a different pen 252 such that each pen 252 contains one and only one of the cells 502 selected at step 102.

FIG. 6 illustrates an example of selecting individual cells 502 in the selection portion 212 of the device 200 (which can be part of step 102) and moving the selected individual cells 502 into isolation pens 252 (step 104). As shown in FIG. 6, the process 100 can select at step 102 a specific, individual cell 502 by trapping a desired cell 502 with a light trap 602 in the selection portion 212 of the device 200. For example, the manipulator 222 (see FIGS. 2A-2C) configured as the OET device 400 of FIGS. 4A and 4B can generate light traps 602 that trap individual cells 502. The OET device 400 can then move the light traps 602 into the pens 252, which moves the trapped cells 502 into the pens 252. As illustrated, each cell 502 can be individually trapped and moved into a holding pen 252.

The light traps 602 can be part of a changing pattern 422 of light projected onto an inner surface 242 of the channel 240 of the micro-fluidic device 200 as discussed above with respect to FIGS. 4A and 4B. Once a selected cell 502 is in a pen 252, the light trap 602 corresponding to that cell 502 can be turned off. The detector 224 can capture images of all or part of the channel 240 including images of the cells 502 and the pens 252, and those images can facilitate trapping and moving specific, individual cells 502 into specific pens 252. The detector 224 and/or the manipulator 222 (e.g., configured as the OET device of FIGS. 4A and 4B) can thus be one or more examples of a means for selecting and moving individual cells 502 from the selection portion 212 into pens 252 in the isolation portion 214 of the device 200.

The manipulator 222 is an example of a means for selecting individual biological cells 502 (e.g., in the selection portion 212 and/or the pens 252 of the device 200) and moving the selected individual cells 502 (e.g., into or out of isolation pens 252). Any configuration (including but not limited to the OET device illustrated in FIGS. 4A and 4B) of the manipulator 222 illustrated, discussed, or disclosed herein is thus an example of means for selecting individual biological cells 502 in the device 200 and/or moving the selected individual cells 502 in the device 200. A globally acting force such as gravity (e.g., applied by means of a tilted or tiltable support for the microfluidic device 200 can be used to assist with moving the cells 502. Alternatively, individual cells 502 that are contained within droplets of aqueous medium can be selected and moved into a holding pen 252 using an OEW device.

As noted above, alternatively, cells 502 can be in the pens 252 prior to step 102, and the process 100 can select at step 102 cells 502 that are in the pens 252 for one of more characteristics generally as discussed above. The process 100 can then, at step 104, move unselected cells 502 out of the pens 252, leaving selected cells 502 in the pens 252.

Figure 8:
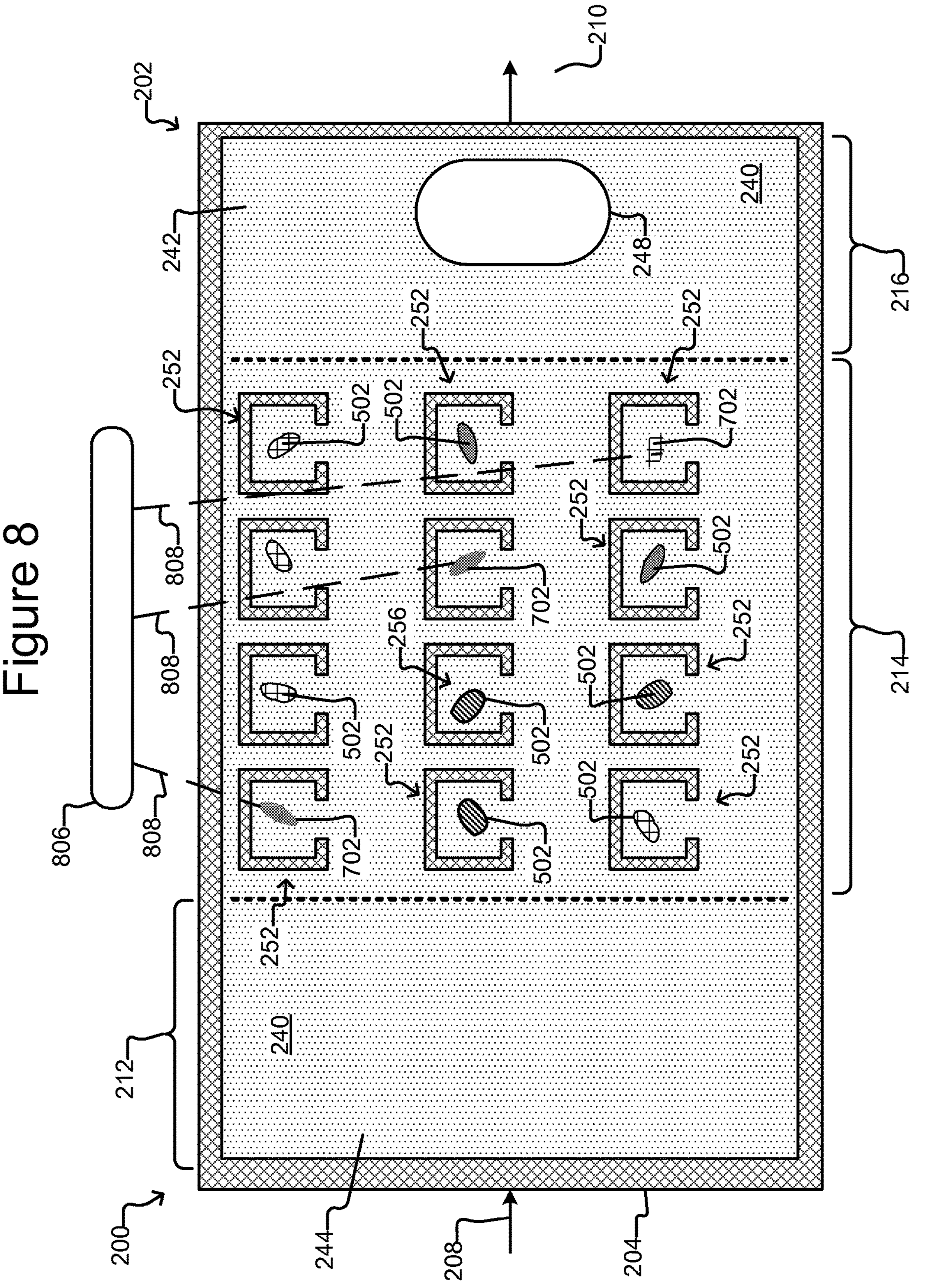
FIG. 8 is an example of lysing cells in the isolation pens of the micro-fluidic device of FIGS. 2A-2C with a lysing mechanism according to some embodiments of the invention.
Figure 9:
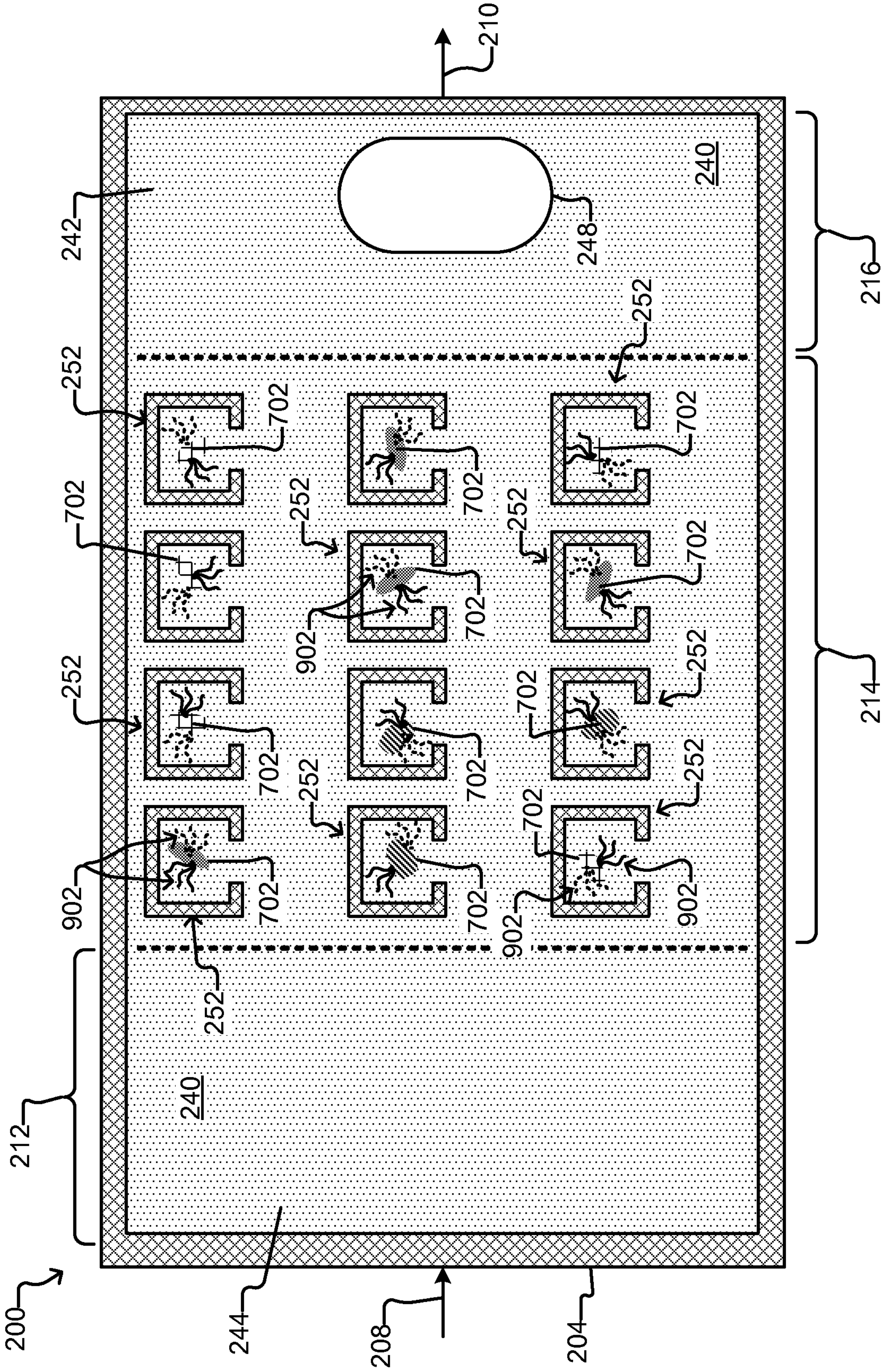
FIG. 9 shows nucleic acid material flowing from the lysed cells into the interior spaces of the isolation pens of the micro-fluidic device of FIGS. 2A-2C according to some embodiments of the invention.

Returning again to FIG. 1, at step 106, the process 100 can lyse cells 502 in the isolation pens 252. FIGS. 7 and 8 illustrate examples of lysing cells 502 in pens 252, which can thus be examples of lysing pens. Cells 502 that are lysed at step 106 are labeled 702 in FIGS. 7-12.

As shown in FIG. 7, cells 502 in isolation pens 252 can be lysed to produce lysed cells 702 by flowing 704 a lysing reagent 706 through the isolation portion 214 of the device 200. For example, the lysing reagent 706 can be flowed from the inlet 208 to the outlet 210 for a sufficient time period for the lysing reagent 706 to enter into the interior spaces 256 of the pens 252 (e.g., by diffusion through the openings 258 of the pens 252) and lyse cells 502 in the pens 252. Although not shown, thereafter medium 244 can be flowed through the isolation portion 214 of the device sufficient to flush the lysing reagent 706 from the device 200. Alternatively, one or more droplets of lysing reagent 706 can be moved into each pen 252 (e.g., using an OEW device) and merged with a droplet containing a cell 502 to be lysed.

Lysing reagent 706 can be any suitable lysis buffer (or combined lysis/nucleic acid binding buffer) known in the art. For example, the lysis buffer can include a buffering agent, a chelating agent, salt, a detergent or chaotropic agent, an RNase inhibitor, a protease, a denaturant, or any combination thereof. The buffering agent can be, for example, a Tris buffer such as TrisHCl (e.g., at a concentration of about 10 mM to about 100 mM). The buffering agent can provide a physiologically-compatible pH (e.g., about pH 7.0 to about pH 8.5). The chelating agent can be, for example, a divalent cation chelating agent, such as EDTA or EGTA (e.g., at a concentration of about 1 mM to about 10 mM). The salt can be, for example, a chloride salt, such as LiCl, NaCl, or KCl (e.g., at a concentration of about 100 mM to about 1 M). The detergent can be, for example, an ionic detergent, such as sodium dodecyl sulfate (SDS), lithium dodecyl sulfate (LiDS), or the like (e.g., at a concentration of about 0.1% to about 1.0%), a non-ionic detergent, such as Triton X-100, NP-40, a Tween detergent (e.g., Tween 20), or the like (e.g., at a concentration of about 0.1% to about 2.0%). The chaotropic agent can, for example, comprise guanidine (e.g., guanidine HCl or guanidine isothiocyanate) or urea (e.g., at a concentration of about 0.1 M to about 6.0 M). The RNase inhibitor can be at a concentration of about 0.1 to 2.0 units per microliter. The protease can be, e.g., Proteinase K or the like (e.g., at a concentration of about 100 ng/ml to about 1 mg/ml). The denaturant can include, for example, formamide or DTT (e.g., at a concentration of about 0.01 M to about 1 M). Thus, in certain embodiments, the lysing reagent 706 can comprise a buffering agent (e.g., Tris HCl), a chloride salt (e.g., NaCl), an ionic and/or non-ionic detergent (e.g., SDS), a protease, and an RNase inhibitor. In other embodiments, the lysing reagent 706 can comprise a buffering agent (e.g., Tris HCl), a chloride salt (e.g., LiCl), a divalent cation chelating agent (e.g., EDTA), a denaturant (e.g., DTT), and an ionic and/or non-ionic detergent (e.g., LiDS).

FIG. 8 illustrates another example of lysing cells 502 in the pens 252 to produce lysed cells 702. As shown, FIG. 8 includes a lysing mechanism 806, which can be part of or separate from the device 200. The lysing mechanism 806 can be controlled to direct lysing beams 808 at one or more of the cells 502 in the pens 252 to produce lysed cells 702. Each lysing beam 808 can comprise sufficient energy to lyse one of the cells 502. The lysing mechanism 806 can be, for example, a laser mechanism, and the lysing beams 808 can comprise laser beams. The lysing mechanism 806 can be controlled (e.g., by the control module 230 of FIG. 2A) to direct a lysing beam 808 at a specific one of the cells 502.

The lysing mechanism 806 can be controlled to lyse selectively individual cells 502 one at a time. For example, the lysing mechanism 806 can be controlled to lyse cells 502 in the pens 252 sequentially one at a time. As another example, the lysing mechanism 806 can be controlled to lyse a subset of more than one but less than all of the cells 502 in the pens 252 substantially in parallel. As yet another example, the lysing mechanism 806 can be controlled to lyse all of the cells 502 in the pens 252 substantially simultaneously.

FIGS. 7 and 8 illustrate examples of lysing cells 502 in the pens 252. Other examples of lysing include applying electroporation, temperature (e.g., heat that exceeds an upper lysing threshold or cold that is less than a lower lysing threshold), electric field energy, or acoustic energy to one or more of the cells 502 in the pens 252. For example, the lysing mechanism 806 can be replaced with a similar mechanism for applying electroporation, electric field energy, or acoustic energy to or controlling the temperature of one or more of the cells 502 sufficiently to lyse the cells 502. Another example of an alternative way to lyse cells 502 is capturing and moving (e.g., with the manipulator 222 of FIGS. 2A-2C) cells 502 into contact with a mechanical piercing device (not shown) such as a knife structure, a spear structure, or the like. Any of the foregoing or other devices and processes can be used to lyse one or more of the cells 502 in the pens 252 at step 106 to produce lysed cells 702.

Regardless of how lysed, the membrane of a lysed cell 702 is sufficiently disrupted that nucleic acid material from the lysed cell 702 is free to flow out of the lysed cell 702 and into the interior space 256 of the corresponding pen 252 (or within an aqueous droplet contained within the corresponding pen 252). An example in shown in FIG. 9, which shows nucleic acid material 902 from lysed cells 702 in pens 252. As noted, the isolation pens 252 can prevent nucleic acid material 902 from a lysed cell 702 in one pen 252 from flowing into and mixing with nucleic acid material 902 from a different lysed cell 702 in another pen 252. The isolation pens 252 can also prevent droplets, materials, elements, or objects (e.g., capture objects 1002 to be discussed below) in one pen 252 for mixing with droplets, materials, elements, or objects in the other pens 252.

The nucleic acid material 902 can comprise, for example, deoxyribonucleic acid (DNA), ribonucleic acid (RNA), or the like. Such DNA can be any type of DNA including mitochondrial DNA (mitDNA), nuclear DNA (nDNA), or exome DNA. Such RNA can be any type of RNA including micro RNA (miRNA), messenger RNA (mRNA), ribosomal RNA (rRNA), small nuclear RNA (rnRNA), or transfer RNA (tRNA).

The lysing mechanism 806 (e.g., a laser) configured to generate and direct lysing energy 808 (e.g., laser beams) at individual cells 502 in the isolation pens 252, an electroporation device configured to electroporate cells 502 in the isolation pens 252, a temperature control device configured to heat or cool cells 502 in the isolation pens 252 sufficiently to lyse the cells 502, or an acoustic device configured to apply sufficient acoustic energy to cells 502 in the isolation panes 252 to lyse the cells 502 are all examples of lysing means for lysing cells 502 in the isolation pens 252.

In some embodiments, the process 100 can, as part of step 106, control the time of lysing of one or more of the cells 502 in the pens 252.

For example, as part of step 106, the process 100 can time the lysing of one or more cells 502 in the pens 252 to correspond to one or more of the characteristics of the cells 502 utilized at step 102 to select the cells 502. Thus, the process 100 can control the timing of the lysing of one or more cells 502 in the pens 252 to correspond to a particular morphology or size of the cells 502 or material composing or secreted from the cells 502 as detected as part of step 102. Thus, for example, one or more cells 502 in the pens 252 having a size in a first size range can be lysed at a first time, then one or more cells 502 in the pens having a size in a second size range (which can be different than the first size range) can be lysed at a second time (which can be different than (e.g., later or earlier in time) than the first time), etc. As another example, cells 502 in the pens 252 having a particular morphology characteristic can be lysed at a first time, then one or more cells 502 in the pens 252 having a different morphology characteristic can be lysed at a second time (which can be different than (e.g., later or earlier in time) than the first time), etc. In certain embodiments, the amount of time that it takes to lyse one or more cells can be, for example about 1 to about 10 minutes (e.g., about 5 to about 10 minutes).

As another example of controlling the timing of lysing at step 106, the process 100 can time the lysing of one or more cells 502 in the pens 252 to correspond to a particular event. For example, step 106 can include monitoring the pens 252 and/or the selection region 212 for a particular event, and the process 100 can then time lysing of one or more cells 502 in the pens 252 from the detected event. Examples of the event can include a change in morphology or secretion or dividing of one or more cells 502 in the pens 252 or the selection region 212. The selection region 212 and/or the pens 252 can be monitored for such events by capturing images of the pens 252 and/or the selection region 212 with the detector 224, and the images can be analyzed by a human operator and/or the control module 230 configured (e.g., programmed with software, microcode, firmware, or the like) to analyze such images generally as discussed above.

The timing of lysing can be controlled by controlling any of the lysing mechanisms discussed above. For example, a human user and/or the control module 230 can control the lysing mechanism 806 to lyse particular cells 502 in the pens 252 at specific times. As another example, although not shown, the device 200 can comprise multiple channels like channel 240, and each of those channels 240 can include a set of isolation pens 252. The lysing time of cells 502 in the pens 252 in each such channel 240 can be controlled by selectively controlling application of lysing to each channel 240. For example, a lysing reagent (e.g., like 706) can be flowed at different times through each individual channel 240. As another example, a lysing temperature, lysing electric field energy, lysing acoustic energy, or the like can be selectively applied at different times to each channel 240.

Figure 10:
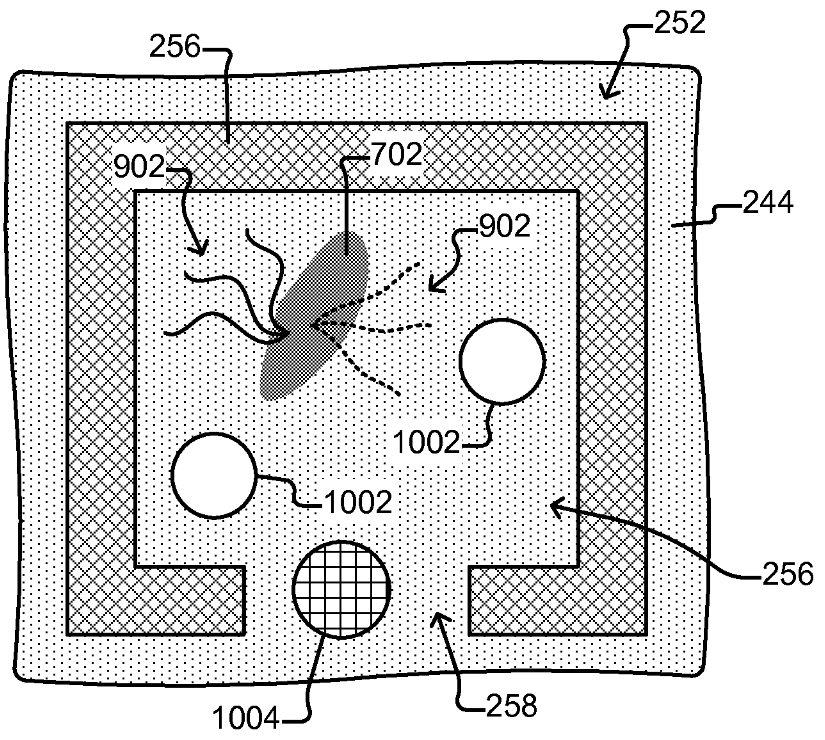
FIG. 10 illustrates an example of capture objects in one of the pens of the micro-fluidic device of FIGS. 2A-2C according to some embodiments of the invention.

Referring again to FIG. 1, at step 108, one or more types of the nucleic acid material from cells lysed at step 106 can be captured with one or more capture objects in the pens. FIG. 10, which depicts one of the pens 252, illustrates an example.

As shown in FIG. 10, one or more capture objects 1002 (two are shown but there can be more or fewer) can be disposed in the interior space 256 of a pen 252 with a lysed cell 702. As will be seen, each such capture object 1002 can be configured to bind a particular type of nucleic acid material 902 from the lysed cell 702 in the pen 252. There can be one or more similar capture objects in each of the pens 252 in the device 200.

Figure 11:
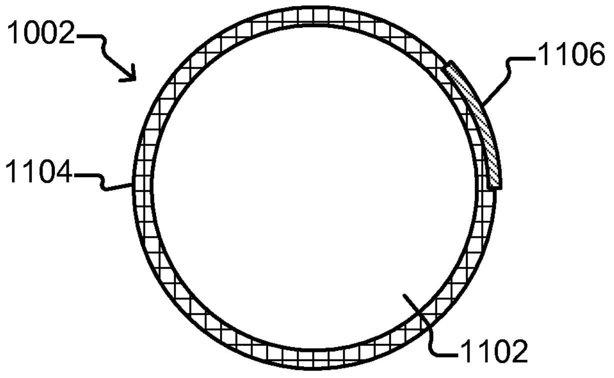
FIG. 11 shows an example configuration of a capture object according to some embodiments of the invention.

FIG. 11 illustrates an example configuration of an object 1002. That is, each capture object 1002 in any of the pens 252 of the device 200 can be configured like the capture object 1002 illustrated in FIG. 11.

As shown in FIG. 11, a capture object 1002 can comprise a base 1102 and a capture material 1104. The base 1102 can be a micro-object such as a micro-bead, a micro-rod, or the like. The base can be, for example, a streptavidin coated bead, a magnetic bead, or the like. The capture material 1104 can comprise a material that binds a specific type of nucleic acid material with a significantly greater (e.g., two, three, five, ten, or more times greater) specificity than any other type of nucleic acid material. For example, the capture material 1104 can bind a specific type of DNA or RNA (e.g., any of the types of DNA or RNA identified above) with a greater (e.g., two, three, five, ten, or more times greater) specificity than any other type of DNA or RNA. Each capture object 1002 in a pen 252 with a lysed cell 702 can have a different capture material 1104 and thus capture a different type of the nucleic acid material (e.g., DNA or RNA) from the lysed cell 702 in the pen 252. Alternatively, each capture object 1002 in a pen 252 with a lysed cell 702 can have the same capture material 1104. In one example, poly-dT oligos can be used to bind mRNA. Alternatively, the oligos can specifically bind to the conserved regions of mRNAs that encode antibody heavy chains and/or light chains.

As also shown in FIG. 11, each capture object 1002 can comprise an identifier 1106, which can comprise a code that uniquely identifies the capture object 1002. Each capture object 1002 in the pens 252 can thus have a unique identifier 1106 so that all of the capture objects 1002 in the device 200 can be uniquely identified one from another.

The identifier 1106 can be any element or material that can uniquely identify a capture object 1002 and facilitate distinguishing one capture object 1002 from another capture object 1002. For example, the identifier 1106 can comprise a biological substance that uniquely identifies the capture object 1002. Synthetic nucleic acid material, such as oligonucleotides (e.g., relatively short, single-stranded DNA or RNA molecules), manufactured to have a unique, user-specified sequence is an example of such an identifier 1106. The identifier 1106 of each of a plurality of capture objects 1002 can have a different such user-specified sequence, allowing the capture objects 1002 to be readily distinguished one from another. As another example, the identifier 1106 can comprise an electronically, optically, or magnetically readable element with a code that uniquely identifies the capture object 1002.

Capture objects 1002 can be placed into the pens 252 as part of step 108 of FIG. 1. Alternatively, capture objects 1002 can be placed into the pens 252 before, during, or after any of steps 102-106. The capture objects 1002 can be placed into pens 252 along with a binding buffer that is conducive to binding between the capture objects 1002 and target nucleic acids.

The binding buffer can be the same as the lysis buffer, as described above. Thus, for example, a combined lysis/binding buffer can be used for both steps 106 and 108 of the method of FIG. 1. In certain embodiments, a suitable lysis/binding buffer can comprise a buffering agent, a chelating agent, salt, a detergent, a denaturant, or any combination thereof. The buffering agent can be, for example, a Tris buffer such as TrisHCl (e.g., at a concentration of about 10 mM to about 100 mM). The buffering agent can provide a physiologically-compatible pH (e.g., about pH 7.0 to about pH 8.5). The chelating agent can be, for example, a divalent cation chelating agent, such as EDTA or EGTA (e.g., at a concentration of about 1 mM to about 10 mM). The salt can be, for example, a chloride salt, such as LiCl, NaCl, or KCl (e.g., at a concentration of about 100 mM to about 1 M). The detergent can be, for example, an ionic detergent, such as sodium dodecyl sulfate (SDS), lithium dodecyl sulfate (LiDS), or the like (e.g., at a concentration of about 0.1% to about 1.0%), a non-ionic detergent, such as Triton X-100, NP-40, a Tween detergent (e.g., Tween 20), or the like (e.g., at a concentration of about 0.1% to about 2.0%). The denaturant can include, for example, formamide or DTT (e.g., at a concentration of about 0.01 M to about 1 M). Thus, for example, the combined lysis/binding buffer can can comprise a buffering agent (e.g., Tris HCl), a chloride salt (e.g., LiCl), a divalent cation chelating agent (e.g., EDTA), a denaturant (e.g., DTT), and an ionic and/or non-ionic detergent (e.g., LiDS).

In certain embodiments, a suitable binding buffer can comprise a buffering agent, a chelating agent, salt, or any combination thereof. The buffering agent can be, for example, a Tris buffer such as TrisHCl (e.g., at a concentration of about 10 mM to about 100 mM). The buffering agent can provide a physiologically-compatible pH (e.g., about pH 7.0 to about pH 8.5). The chelating agent can be, for example, a divalent cation chelating agent, such as EDTA or EGTA (e.g., at a concentration of about 1 mM to about 10 mM). The salt can be, for example, a chloride salt, such as LiCl, NaCl, or KCl (e.g., at a concentration of about 100 mM to about 1 M). Thus, for example, the binding buffer can comprise a buffering agent (e.g., Tris HCl), a chloride salt (e.g., LiCl), and a divalent cation chelator (e.g., EDTA).

Specific individual capture objects 1002 can be placed in each of the pens 252, for example, in the same way selected cells 502 are placed into the pens 252: capture objects 1002 can be loaded through the inlet 208 into the selection portion 212 of the device 200, and specific individual capture objects 1002 can be individually trapped with a light trap (not shown) and moved into a specific pen 252 generally like a selected cell 502 can be trapped by a light trap 602 and moved into a pen 252 as discussed above. Alternatively, capture objects 1002 can be contained within aqueous droplets and the droplets can be moved into the pens 252, for example, using OEW. The individual capture objects 1002 can be moved into a pen 252, and such movement can be in parallel, serially one at a time, or in part in parallel and in part serially.

As noted, each of the one or more objects 1002 in a pen 252 with a lysed cell 702 can have a different capture material 1104 and thus capture a different, specific type of nucleic acid material from the lysed cell 702. The process 100 can thus capture any one or more specific types of nucleic acid material from the lysed cell 702 in a pen 252.

As also noted, the enclosure 254 of each pen 252 can be configured to keep the nucleic acid material 902 within the interior space 256 of the pen 252. Alternatively or in addition, a blocking object 1004 can be placed generally in the opening 258 of a pen 252, for example, as illustrated in FIG. 10. The blocking object 1004 can be generally similar to a capture object 1002 except that the blocking object 1004 can be configured to bind with a relatively high specificity most or all of the different types of nucleic acid material 902 from the lysed cell 702 in the pen 252. In still other alternatives, oil used for an OEW-type configuration can be located in the space between isolation pens 252 (e.g., a channel) and optionally in the opening 258 of the pens 252. The blocking object 1004 or oil (not shown) can thus further prevent nucleic acid material 902 from a lysed cell 702 in a pen 252 from escaping the pen 252 and mixing with nucleic acid material 902 in another pen 252.

The blocking object 1004 can be similar to a capture object 1002. For example, the blocking object 1004 can comprise a base (not shown but can be like base 1102 of FIG. 11) and a capture material (not shown but can be like capture material 1104). As noted, however, the capture material (not shown) of the blocking object 1004 can be configured to bind most or all of the nucleic acid material 902 from a lysed cell 702 in the pen 252.

In the examples illustrated in FIGS. 7-10, the outer membrane of a cell 502 in a pen 252 and any number from zero to all of the membranes of elements internal to the cell 502 can be lysed at step 1006 of FIG. 1. Each lysed cells 702 can thus have its outer membrane and none, some, or all of any internal membranes inside the cell 702 lysed at step 106, and the nucleic acid material 902 can comprise some or all of the nucleic acid material 902 from anywhere inside a lysed cell 702. As discussed above, at step 108, specific types of the nucleic acid material 902 in the pen 252 can be captured with one or more capture objects 1002 in the pen 252.

Figure 12A:
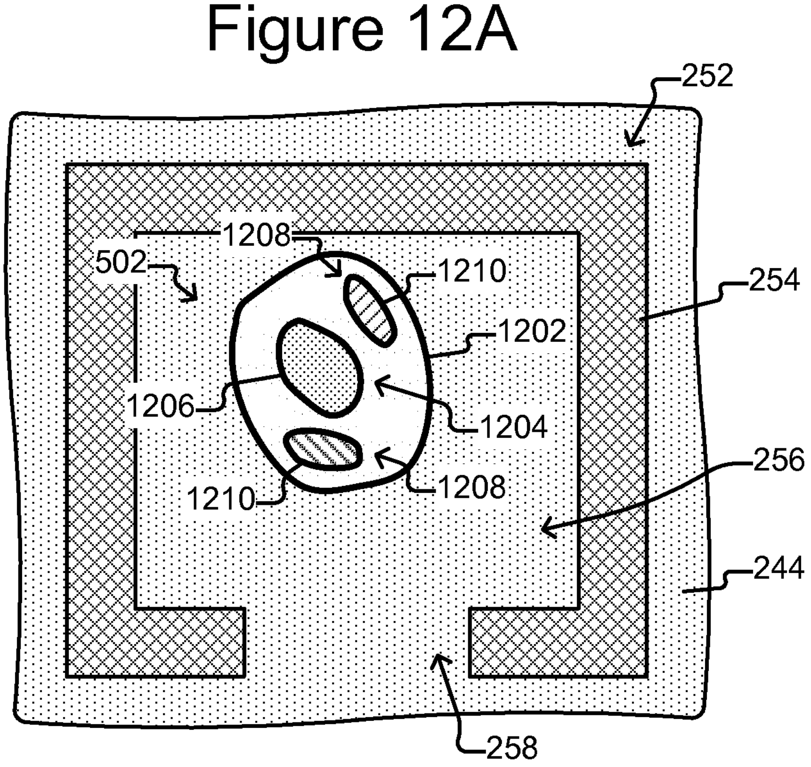
FIG. 12A illustrates an example of a cell in a pen of the micro-fluidic device of FIGS. 2A-2C showing the outer membrane of the cell and examples of elements internal to the cell.
Figure 12B:
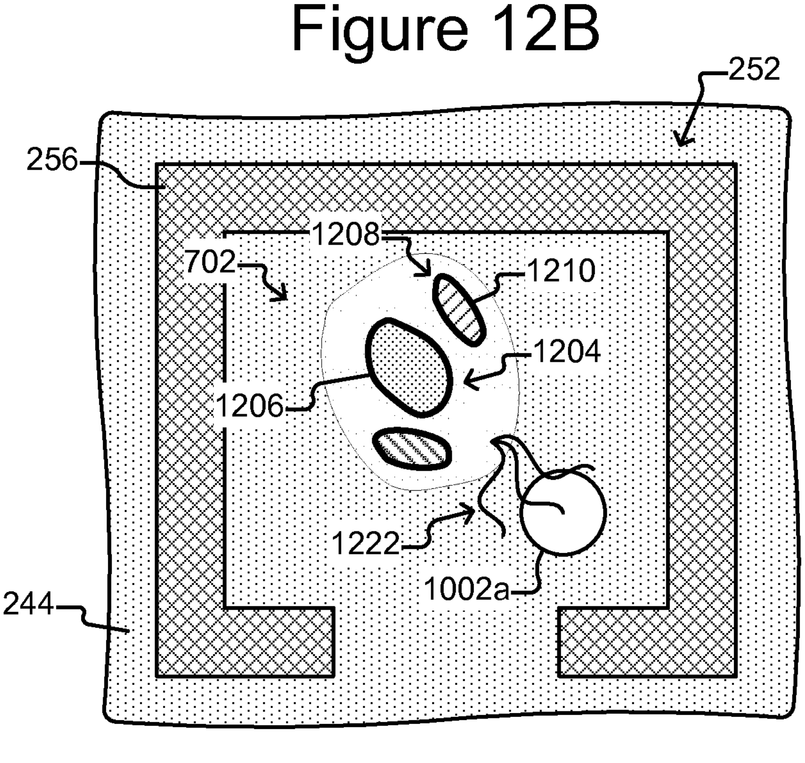
FIG. 12B shows an example of lysing the cell of FIG. 12A according to some embodiments of the invention.

FIGS. 12A and 12B illustrate an example in which step 106 of FIG. 1 can be performed such that only a selected one or more of the membranes of a cell 502, but not all of the membranes, are lysed.

FIG. 12A (which, like FIG. 10, shows one of the pens 252 in the device 200) illustrates example components of a cell 502 in the pen 252. Components of the cell 502 can include a nucleus 1204 and organelles 1208 (two are shown but there can be more or fewer). As is known, an outer membrane 1202 bounds the cell 502, a nuclear membrane 1206 bounds the nucleus 1204, and a mitochondrial membrane 1210 bounds each organelle 1208.

As shown in FIG. 12B, rather than lyse all of the membranes 1202, 1206, 1210 of the cell 502 in the pen 252 at step 106, one or more but less than all of the membranes 1202, 1206, 1210 can be lysed at step 106. In the example, illustrated in FIG. 12B, the outer membrane 1202, but not the nuclear membrane 1206 or any of the mitochondrial membranes 1210, of the cell 502 is lysed at step 106. The released nucleic acid material 1222 will thus not include nucleic acid material from inside the nucleus 1204 or the organelles 1208. Thus, in the example illustrated in FIG. 12B, the released nucleic acid material 1222 can be RNA (e.g., any of the types of RNA identified above).

Step 108 can then be performed generally as discussed above to capture one or more of the types of nucleic acid material 1222 released from the now lysed cell 702. For example, as shown in FIG. 12B, one or more capture objects 1002*a* (one is shown but there can be more) configured to capture one or more types of the nucleic acid material 1222 released from the lysed cell 702 can be in the pen 252.

Figure 12C:
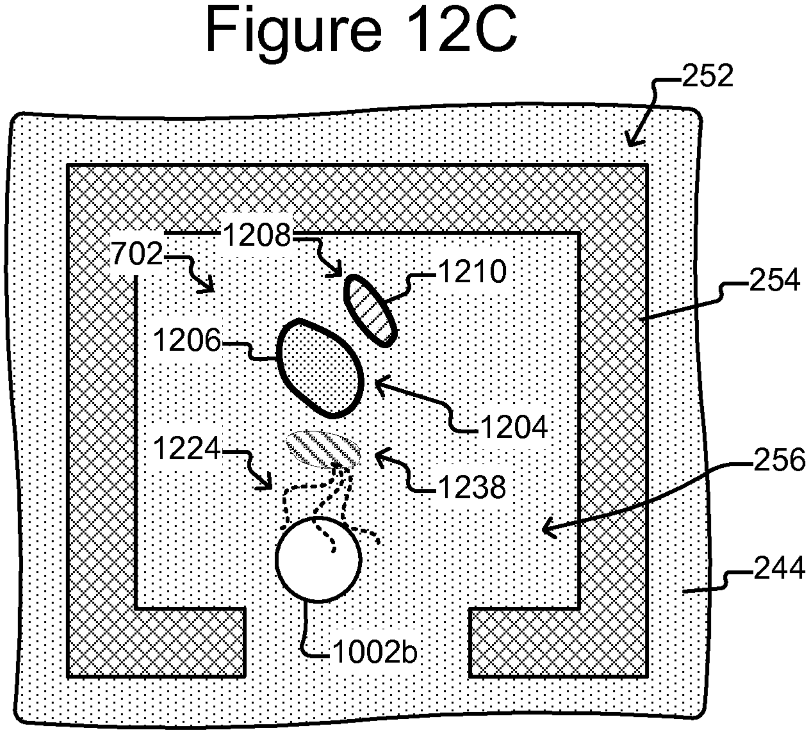
FIG. 12C is an example of lysing one of the internal elements of the cell of FIG. 12A according to some embodiments of the invention.
Figure 12D:
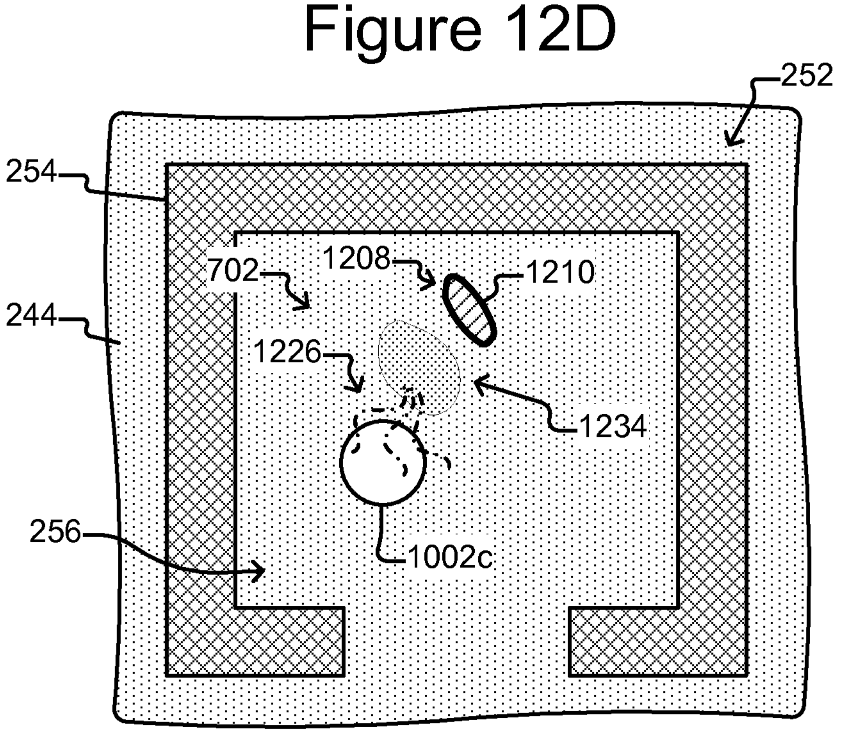
FIG. 12D shows an example of lysing the nucleus of the cell of FIG. 12A according to some embodiments of the invention.

As illustrated in FIGS. 12C and 12D, steps 106 and 108 can be repeated one or more times to lyse one or more additional membranes of the now lysed cell 702 in the pen 252 and thus release and capture additional types of nucleic acid material released as each additional membrane is lysed.

In the example illustrated in FIG. 12C, the mitochondrial membrane 1210 of one of the organelles 1208 is lysed at a repetition of step 106 of FIG. 1, which can release nucleic acid material 1224 from the now lysed organelle 1238. (A lysed organelle 1208 is labeled 1238 in FIG. 12C.) The released nucleic acid material 1224 can comprise nucleic acid material, such as mtDNA, such as is typically found in organelles. Step 108 of FIG. 1 can then be repeated generally as discussed above to capture one or more types of the nucleic acid material 1224 released from the lysed organelle 1238. For example, as shown in FIG. 12C, one or more capture objects 1002*b* (one is shown but there can be more) configured to capture one or more types of the nucleic acid material 1224 released from the lysed organelle 1238 can be in the pen 252. In this example in which an organelle 1208 is lysed before lysing the nucleus 1204, highly enriched mtDNA from the lysed organelle 1208 can be captured because there is no free nuclear DNA from the nucleus 1204 in the interior space 256 of the pen 252.

In the example illustrated in FIG. 12D, the nuclear membrane 1206 of the nucleus 1204 can be lysed at another repetition of step 106 of FIG. 1, which can release nucleic acid material 1226 from the now lysed nucleus 1234. (The lysed nucleus 1204 is labeled 1234 in FIG. 12D.) The released nucleic acid material 1226 can comprise nucleic acid material, such as various types of DNA, typically found in the nucleus of a cell. Step 108 can then be repeated again generally as discussed above to capture one or more types of the nucleic acid material 1226 released from the lysed nucleus 1234. For example, as shown in FIG. 12D, one or more capture objects 1002*c* (one is shown but there can be more) configured to capture one or more types of the nucleic acid material 1226 released from the lysed nucleus 1234 can be in the pen 252.

Figure 13:
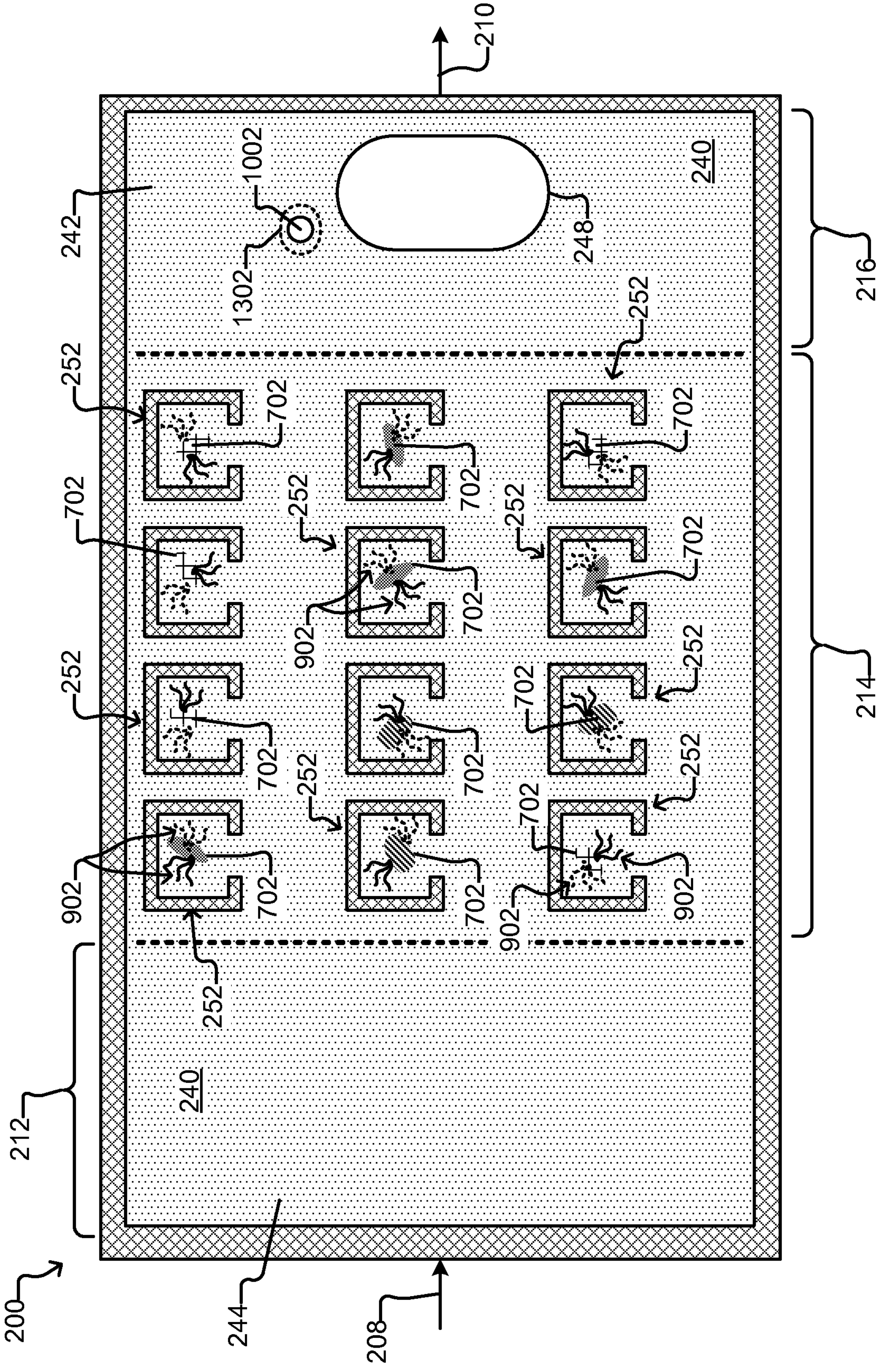
FIG. 13 is an example of selecting and moving capture objects from the isolation pens to the export portion of the micro-fluidic device of FIGS. 2A-2C according to some embodiments of the invention.

In the examples illustrated in FIGS. 12A-12D, the membranes 1202. 1206, 1208 can be lysed and the capture objects 1002*a*, 1002*b*, 1002*c* can be moved into the pen 252 in any manner illustrated or discussed above. Moreover, each capture object 1002*a*, 1002*b*, 1002*c* can be removed from the pen 252 (e.g., generally as shown in FIG. 13 and discussed below) at the end of each repetition of step 108, or all of the capture objects 1002*a*, 1002*b*, 1002*c* can be removed (e.g., generally as shown in FIG. 13 and discussed below) from the pen 252 after the last repetition of step 108.

Although FIGS. 12C and 12D illustrate lysing an organelle 1208 and then lysing the nucleus 1204, other orders are possible. For example, the nucleus 1204 can be lysed (as illustrated in FIG. 12D) before lysing an organelle 1208 (as illustrated in FIG. 12C). As another example, multiple organelles 1208 can be lysed (each as shown in FIG. 12C), and the nuclear membrane 1206 can be lysed (as shown in FIG. 12D) between the lysing of two of the organelles 1208.

Although FIGS. 12A-12D illustrate only one pen 252 of the device 100, the lysing and capturing with capture objects 1002 illustrated in those figures can also be performed in others of the pens 252 in the device 100. Also, although the example cell 502 in FIGS. 12A-12D is illustrated as having a nuclear membrane 1206 and thus being an eukaryote cell, the cells 502 illustrated in the drawings and discussed herein can be other types of cells such as prokaryote cells.

Returning again to FIG. 1, at step 110, the process 100 can remove one or more of the capture objects 1002 from one or more of the pens 252. FIG. 13 illustrates an example in which light cages 1302 can trap capture objects 1002 in the pens 252 and move the capture objects 1002 into the export portion 216 of the device 200. (Any of the DEP devices discussed or mentioned above, including an OET device configured as illustrated in FIGS. 4A and 4B or, alternatively, and OEW device, is thus an example of a means for selecting individual capture objects 1002 (or droplets containing such capture objects) in the isolation pens 252 of the device 200 and moving the selected capture objects 1002 out of the isolation pens 252.) For example, the capture objects 1002 can be moved to the staging area 248 of the export mechanism 228 and exported from the device 200 through the passage 246. The foregoing can be performed in any manner, for example, disclosed in the aforementioned US patent application serial no. U.S. patent application Ser. No. 14/520,510 (filed Oct. 22, 2014). Alternatively, capture objects 1002 can be exported from the device 200 through an outlet 210. As yet another alternative, capture objects 1002 removed from the pens 252 at step 110 can be stored and/or further processed at other locations in the device 200.

The process 100 of FIG. 1 can thus identify and select from a group of cells in a micro-fluidic device 200 specific individual cells 502 determined to have one or more particular characteristic, and the process 100 can place the selected cells 502 individually into isolation pens 252 in the device 200 such that each of the pens 252 contains only one of the selected cells 502. The process 100 can then extract nucleic acid material from a single cell 502 in one of the pens 252 and capture with one or more capture objects 1002 in the pen 252 one or more specific types of nucleic acid material (e.g., any one or more of the types of DNA or RNA identified above) from the single cell 502. Alternatively, the process 100 can place more than one cell 502 in a pen 252 and/or a single cell 252 in a pen can grow and multiple into multiple such cells in a pen 252. Regardless, the process 100 can then individually remove capture objects 1002, and thus the nucleic acid material captured by the capture objects 1002, from the pens 252 and export the capture objects 1002 from the device 200, store the capture objects 1002 in other locations in the device 200, or further process the capture objects 1002 in the device 200.

As noted, each capture object 1002 can comprise a unique identifier 1006, which can facilitate correlating the nucleic acid material on each capture object 1002 with the cell 502 from which the nucleic acid material originated. For example, the control module 230 can be programmed to maintain a digital record (e.g., stored in the memory 234) of each of the unique identifiers 1106 of the capture objects 1002 and, for each capture object 1002, information regarding nucleic acid material captured by the capture object 1002. For example, the controller 230 can store in the memory 234 any of the following information associated with the unique identifier 1106 of a particular capture object 1002: an identification of the particular pen 252 in which the nucleic acid material was captured, characteristics of the cell 502 from which the nucleic acid material was captured, the type of nucleic acid material captured, processing conditions in which the nucleic acid material was captured, and/or the like. The controller 230, programmed as described above, can thus be an example of a means for storing a correlation between the capture objects and data regarding the nucleic acid material captured by each capture object.

Indeed, the control module 230 of FIG. 2A can be configured (e.g., programmed with software, firmware, microcode, or the like; hardwired; or the like) to control or can provide for control by a human operator of some, most, or all of the process 100. For example, the control module 230 can be configured to control operation of the manipulator 222, the detector 224, the flow controller 226, and/or the output mechanism 228 to carry out any or all of the steps 102-110 of the process 100 in any way described above.

The process 100 shown in FIG. 1 and the operation of the process 100 illustrated in FIGS. 5-13 are examples only, and variations are contemplated. For example, one or more of the steps 102-110 can be performed in a different order than shown in FIG. 1. As another example, not all of the steps 102-110 need be performed, and the process 100 can thus comprise less than all of the steps 102-110. As yet another example, steps in addition to steps 102-110 can be performed. For example, one or more washing steps can be performed before, during, or after any of the steps 102-110 to, for example, wash one or more of the capture objects 1002. As still another example, although process 100 is illustrated and discussed above as placing only one cell 502 in a pen 252 and then extracting and capturing nucleic acid material from only a single cell 502 in each pen 252, the process 100 can alternatively place multiple cells 502 in a pen 252 and extract and capture nucleic acid material from the multiple cells in the pen 252. As yet another example, an individual cell 502 can be placed in a pen 252 and allowed to grow and multiple into multiple cells prior to releasing and capturing nucleic acid material from one or more of the cells 502 thus grown and then lysed. Additional cells 502 that are not lysed can be exported from the pen 252 as living progeny of the lysed cell 702.

Figure 14:
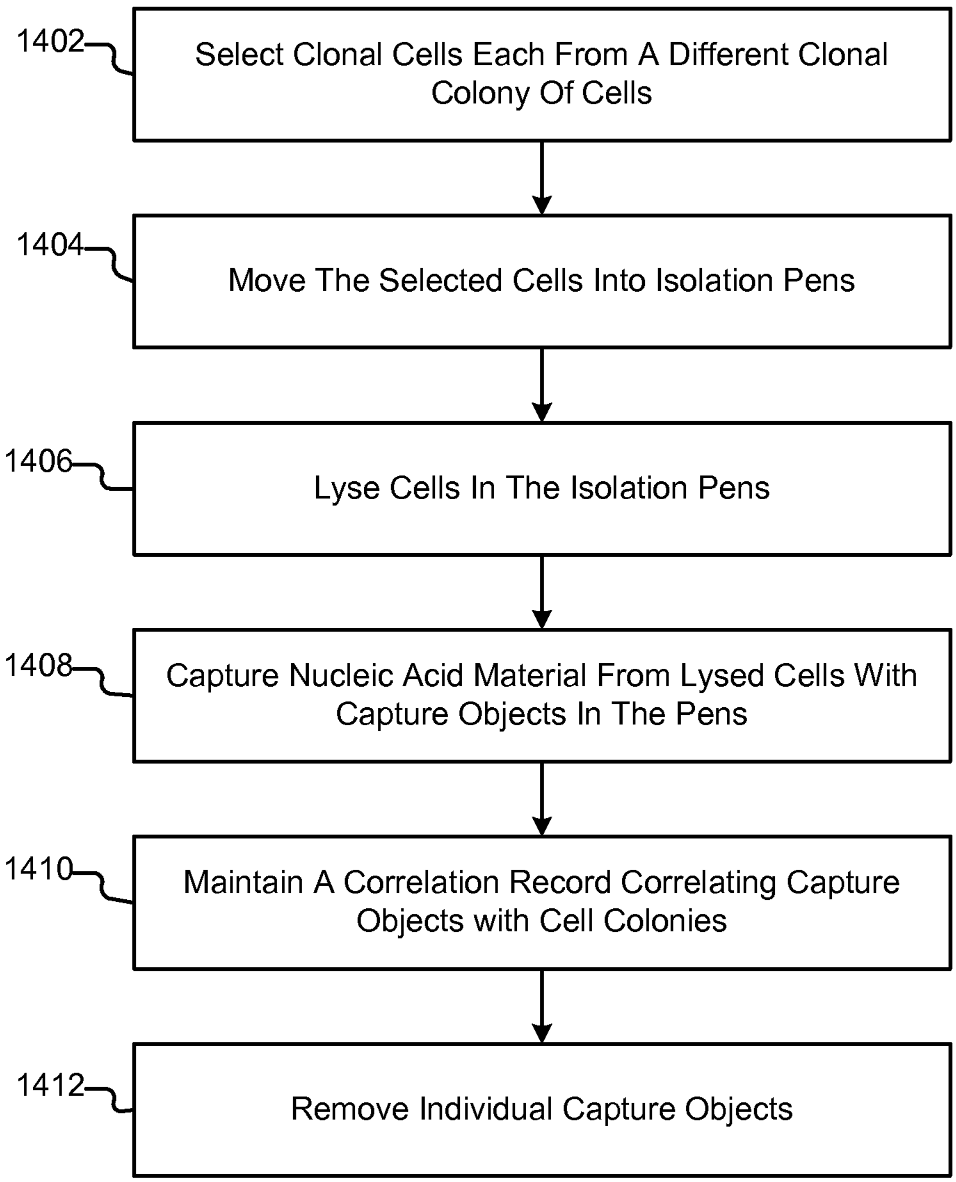
FIG. 14 is an example of a process for selectively capturing nucleic acid material from clonal biological cells according to some embodiments of the invention.

FIG. 14 illustrates another example of a process 1400 for extracting and capturing nucleic acid from biological cells. As will be seen, the process 1400 can move selected clonal cells from clonal cell colonies into isolation pens, where the process 1400 can lyse the clonal cells and capture with capture objects in the pens nucleic acid released from the cells. The process can also store a correlation record correlating each such capture object to the clonal cell colonies from which the clonal cell whose nucleic acid is captured by the capture object was taken.

Figure 15:
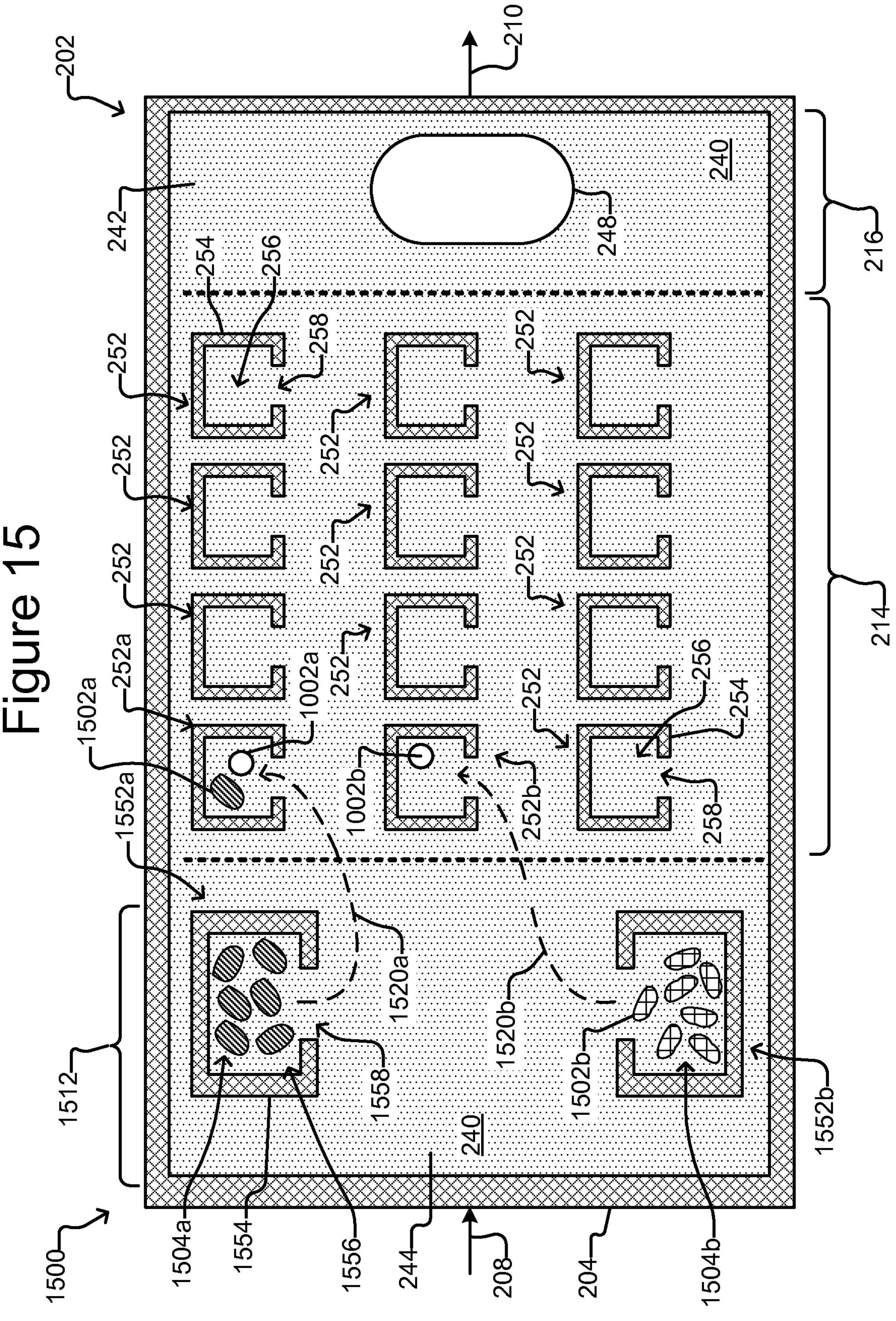
FIG. 15 illustrates an example of selecting individual clonal biological cells from different clonal colonies in a micro-fluidic device and moving the selected cells into isolation pens in the device according to some embodiments of the invention.

FIG. 15 shows a top cross-sectional view of an example of a micro-fluidic device 1500 on which the process 1400 can be performed. The device 1500 can be generally the same as the device 200 (e.g., as illustrated in FIGS. 2A-2C including any variation illustrated in any of FIGS. 3, 4A, 4B, 7, and 8) except device 1500 can include a culturing portion 1512 rather than (or in addition to) the selection portion 212. As shown, there can be culturing pens 1552 (two are shown but there can be more or fewer) in the culturing portion 1512. Other than the culturing pens 1552, the culturing portion 1512 can be generally the same as or similar to the selection portion 212 of FIGS. 2A-2C including any variation illustrated or described herein.

Examples of the culturing pens 1552 are illustrated in FIG. 15. As shown, each culturing pen 1552 can be generally similar to an isolation pen 252. For example, a culturing pen 1552 can comprise an enclosure 1554 that defines an interior space 1556 and an opening 1558 from the channel 240 to the interior space 1556. The enclosure 1554, interior space 1556, and opening 1558 can be generally similar, respectively, to the enclosure 254, interior space 256, and interior space 256 (including any variation illustrated or described herein) of the device 200 of FIGS. 2A-2C. For example, the enclosure 1554 can comprise any of the materials mentioned above with respect to the enclosure 254. As another example, the opening 1558 of each isolation pen 1552 can be sized and positioned to allow for the natural exchange of liquid medium 244 in a pen 1552 and liquid medium 244 flowing past the opening 1558 of the pen 1552. Otherwise, however, the enclosures 1554 can enclose the interior spaces 1556 of the culturing pens 1552 sufficiently to prevent biological material, cells, or objects in the interior space 1556 of one culturing pen 1552 from mixing with such biological material, cells, or objects in the interior space 1556 of any another culturing pen 1552.

The number, pattern, and configuration of the culturing pens 1552 illustrated in FIG. 15 is an example, and variations are possible. For example, each culturing pen 1552 can instead be like the pens 352 illustrated in FIG. 3.

Generally as illustrated in FIG. 15, a colony of clonal cells 1504 can be cultured in one or more of the culturing pens 1552. In the example of FIG. 15, a first colony 1504*a* of clonal cells 1502*a* is cultured in a first culturing pen 1552*a*, and a second colony 1504*b* of clonal cells 1502*b* is cultured in a second culturing pen 1552*b*. As noted, there can be more than two culturing pens 1552, and a different colony 1504 of clonal cells 1502 can be cultured in each of any number of the culturing pens 1552.

Each such colony 1504 can be created in one of the culturing pens 1552 by placing a parent cell into the pen 1552 and allowing the parent cell to produce daughter cells in the pen 1552. For example, the parent cell and resulting daughter cells can be cultured in a pen 1552 by providing a flow of nutrients in a flow of medium 244 in the channel 240 past the opening 1558 of the culturing pen 1552. Such nutrients can flow into and cell waste can flow out of the pen 1552 by, for example, diffusion of medium 244 through the opening 1558.

All of the cells 1502 in a particular culturing pen 1552 can thus consist solely of the parent cell placed into the pen 1552 and daughter cells produced by or from the parent cell. Thus, for example, all of the cells 1502*a* in the first colony 1552 in the first culturing pen 1552*a* can be either a parent cell or progeny of the parent cell. The first colony 1504*a* can thus be a clonal colony, and all of the cells 1502*a* of the first colony 1504*a* can be clonal cells. Similarly, all of the cells 1502*b* in the second colony 1504*b* in the second culturing pen 1552*b* can be either a parent cell or progeny of the parent cell. The second colony 1504*b* can thus be a clonal colony, and all of the cells 1502*b* of the second colony 1504*b* can be clonal cells.

Referring now to FIG. 14, at step 1402, the process 1400 can select individual clonal cells 1502 from the colonies 1504 in the culturing pens 1552 in the device 1500, and at step 1404, the process 1400 can move the selected individual clonal cells 1502 into isolation pens 252 in the isolation portion 214 of the device 1500. FIG. 15 illustrates an example. As shown in FIG. 15, a single, individual cell 1502*a* from the first colony 1504*a* can be selected in and moved 1520*a* from the first culturing pen 1552*a* to a first one of the isolation pens 252*a*. In certain embodiments, the isolation portion 214 of the device 1500 can be configured for OEW and the movement of individual cell 1502*a* from the first colony 1504*a* can involve creating a droplet of aqueous medium containing the individual cell 1502*a* in an oil medium, and moving the droplet into the isolation pen 252*a*. As previously noted, the isolation pens 252 can be examples of lysing pens. Similarly, a single, individual cell 1502*b* from the second colony 1504*b* can be selected in and moved 1520*b* from the second culturing pen 1552*b* to a second one of the isolation pens 252*b*. As noted, there can be more than two such culturing pens 1552, and a clonal cell 1502 from a clonal cell colony 1504 can be thus placed in a plurality (e.g., all) of the isolation pens 252. For example, one and only one clonal cell 1502 can be placed in each of a plurality of the isolation pens 252, and each such clonal cell 1502 can be from a different clonal cell colony 1504 in a different culturing pen 1552. Alternatively, more than one clonal cell 1502 can be placed in an isolation pen 252, but all of the clonal cells 1502 placed in any one isolation pen 252 can be from the same clonal cell colony 1504.

Each clonal cell 1502 can be selected from its cell colony 1504 randomly or using any selection criteria discussed above with respect to step 102 of FIG. 2. The clonal cells 1502 can be selected in and moved from the culturing pen 1552 in any way discussed above with respect to step 104. For example, each clonal cell 1502 can be trapped with a light trap (not shown in FIG. 15) like light trap 602, which can be generated and manipulated as discussed above with respect to FIG. 6.

Alternatively, or in addition, OEW can be used to create a droplet of aqueous medium that contains the clonal cell 1502. In still other alternatives, the cell colonies 1504 can be located outside of the device 1500, and individual clonal cells 1502 from the colonies 1504 can be imported into the device 1500 (e.g., through the inlet 208). Step 1402 can thus be skipped or left out of the process 1400. Once imported into the device 1500, the clonal cells 1502 can be selected and moved into the isolation pens 252 (e.g., generally as shown in FIGS. 5 and 6).

Regardless, after steps 1402 and/or 1404, one or more clonal cells 1502 are now in each of a plurality of the isolation pens 252 of the device 1500, and the one or more clonal cells 1502 in each pen 252 can be from the same clonal colony 1504. As will be seen, the cells 1502 can then be lysed at step 1406, and released nucleic acid material from the lysed cells 1502 can be captured at step 1408. As discussed below, steps 1406 and 1408 can be performed generally like steps 106 and 108 of FIG. 1.

For example, at step 1406, cells 1502 in the isolation pens 252 can be lysed to produce lysed cells (not shown in FIG. 15). Cells 1502 can be lysed in the isolation pens 252 in any of the ways discussed above with respect to step 106 for lysing cells 502 in the isolation pens 252. For example, one or more cells 1502 can be lysed in the isolation pens 252 as illustrated in FIG. 7 or FIG. 8 or in any alternative discussed above. Lysing at step 1406 can include lysing any one or more of the membranes of the cells 1502 (sequentially and/or substantially simultaneously) generally as illustrated in FIGS. 7, 8, and/12A-12D. Generally as illustrated in FIGS. 9 and 12A-12D, lysing at step 1502 can release nucleic acid material from the cells 1502 into interior spaces 256 of the isolation pens 252.

At step 1408, one or more types of the nucleic acid material from cells 1502 lysed at step 1406 can be captured with one or more capture objects 1002 in the pens 252. Step 1408 can be performed in the same way as step 108 is performed including any variation as illustrated and discussed herein. For example, one or more specific types of nucleic acid material released from the lysed cells 1502 can be captured in the isolation pens 252 with one or more capture objects 1002 in the pens 252 as discussed above with respect to step 108.

At step 1410, the process 1400 can create and/or maintain a correlation record correlating each capture objects 1002 in the isolation pens 252 to the cell colony 1504 from which the cell 1502 whose nucleic acid material is captured by the capture object 1002 originated. For example, for each capture object 1002 in the isolation pens 252, the correlation record can correlate a unique identifier (e.g., the identifier 1106 shown in FIG. 11) of the capture object 1002 with any of the following information about the cell 1502 whose nucleic acid material was captured by the capture object 1002: the identity (e.g., location such as the culturing pen 1552) of the clonal cell colony 1504 from which the cell 1502 was taken, one or more characteristics of the cell 1502, and/or the like.

FIG. 15 shows a first capture object 1002*a* in the first isolation pen 252*a* with the first cell 1502*a* from the first cell colony 1504*a*. After the first cell 1502*a* is lysed at step 1406, the first capture object 1002*a* can thus capture nucleic acid material released from the first cell 1502*a*. Similarly, a second capture object 1002*b* in the second isolation pen 252*b* can capture nucleic acid material released after the second cell 1502*b* is lysed. The correlation record created at step 1410 of FIG. 10 can thus comprise a unique identifier of the first capture object 1002*a* correlated with an identification of the first cell colony 1504*a* and/or its culturing pen 1552*a*, and the correlation record can also include a unique identifier of the second capture object 1002*b* correlated with an identification of the second cell colony 1504*b* and/or its culturing pen 1552*b*. In some embodiments, the control module 230 can be programmed (e.g., with machine readable instructions (e.g., software, firmware, or microcode) and/or hardwired circuitry) to create, store (e.g., in the memory 234), and maintain (e.g., update) such a correlation record.

At step 1412, the process 1400 can remove one or more of the capture objects and thus the nucleic acid material captured by the capture objects, from one or more of the isolation pens 252. Step 1412 can be performed generally like step 110 of FIG. 1 including any variation thereof illustrated or discussed herein.

The process 1400 is an example only, and variations are contemplated. For example, one or more of the steps 1402-1412 can be performed in a different order than shown in FIG. 14. As another example, not all of the steps 1402-1412 need be performed, and the process 1400 can thus comprise less than all of the steps 1402-1412. As yet another example, steps in addition to steps 1402-1412 can be performed. For example, one or more washing steps can be performed before, during, or after any of the steps 1402-1412 to, for example, wash one or more of the capture objects. Although specific embodiments and applications of the invention have been described in this specification, these embodiments and applications are exemplary only, and many variations are possible.

EXAMPLES

Example 1

Cell Lysis in Pens

To test cell lysis in isolation pens of a microfluidic device, cells were loaded into isolation pens, a lysis buffer was flowed through the device, and cell lysis was monitored using Calcien AM stain. The lysis buffer was as follows:

RNase inhibitor: 2 units/microliter;
NaCl: 0.135 M;
Tris-HCl (pH 8.0): 9 mM;
Dithiothreitol (DTT) 4.5 mM; and
SDS: 1%.

Figures 16A, 16B, 16C, 16D:
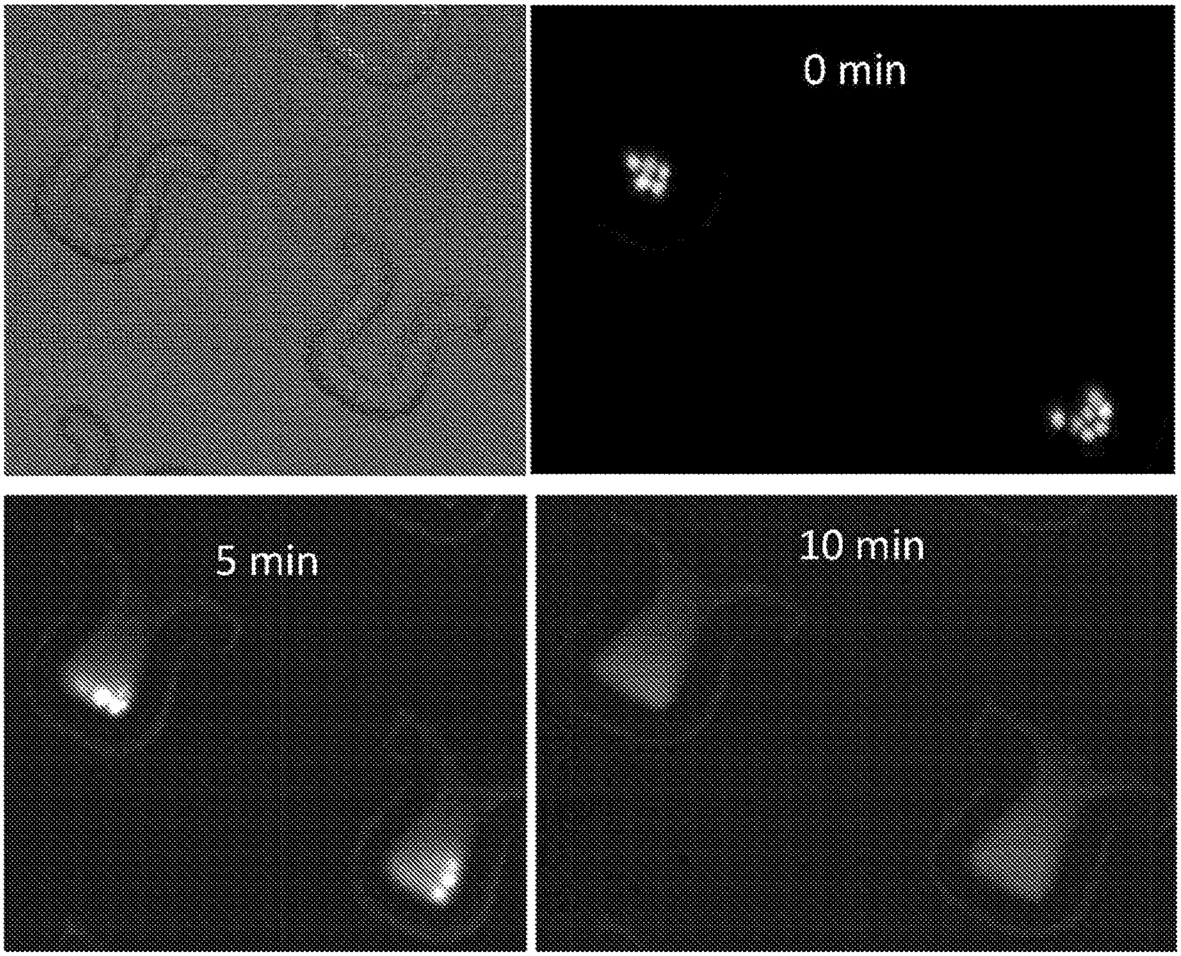
FIGS. 16A-D are images of cells being lysed within isolation pens in a microfluidic device.

As shown in FIGS. 16A-D, cells loaded into the pens (FIG. 16A) are detectable using Calcien AM at t=0 minutes after introduction of the lysis buffer (FIG. 16B). At 5 minutes after introduction of the lysis buffer, the cells are still largely intact but starting to lyse (FIG. 16C). At 10 minutes after introduction of the lysis buffer, cell lysis appears complete (FIG. 16D).

Any of the foregoing components of the lysis buffer can be substituted with equivalent buffers, salts, and chelating agents, as understood by persons skilled in the art.

Example 2

Binding Conditions

Following lysis of cells in isolation pens of a microfluidic device (e.g., as described in Example 1), binding of target nucleic acids to capture objects can be performed by flowing a binding buffer through the microfluidic device while the capture objects are in the presence of cell lysate. The binding buffer can be as follows:

Tris-HCl (pH 7.5): 20 mM;
LiCl: 1.0 M; and
EDTA: 2 mM.

Any of the foregoing components of the binding buffer can be substituted with equivalent buffers, salts, and chelating agents, as understood by persons skilled in the art.

Example 3

Use of a Combined Lysis/Binding Buffer

As an alternative to using separate lysis and binding buffers, cell lysis and nucleic acid capture can be accomplished using a combined lysis/binding buffer. Thus, cell can be loaded into isolation pens in a microfluidic device, and a combined lysis/binding buffer can be flowed through the device for a sufficient time to achieve cell lysis. The lysis/binding buffer can be flowed through prior to, at substantially the same time, or after capture objects are disposed adjacent to the cells that are to be lysed. The combined lysis/binding buffer can be as follows:

Tris-HCl (pH 7.5): 100 mM;
LiCl: 500 mM;
EDTA: 10 mM;
LiDS: 1%; and
DTT: 5 mM.

Any of the foregoing components of the combined lysis/binding buffer can be substituted with equivalent buffers, salts, and chelating agents, as understood by persons skilled in the art.

We claim:

1. A process of capturing nucleic acid material from an individual biological cell, said process comprising:

placing an individual biological cell into one of a plurality of isolation pens in a micro-fluidic device; the micro-fluidic device comprising:

an electrode activation substrate comprising dielectrophoresis (DEP) electrodes at a surface of said substrate, wherein each said DEP electrode is configured to be selectively activated and deactivated; and a micro-fluidic structure disposed on the electrode activation substrate wherein the micro-fluidic structure, at least in part, defines the plurality of isolation pens and a micro-fluidic channel configured to contain a flow of a first liquid medium flowing in a direction from an inlet to an outlet of the micro-fluidic structure; wherein each isolation pen of said plurality of isolation pens comprises a single opening configured to open to the micro-fluidic channel so as to permit exchange between a second liquid medium in the isolation pen with the first liquid medium flowing through the micro-fluidic channel by diffusion;

wherein an interior space of the isolation pen is sufficiently enclosed to prevent biological cells or capture objects in that interior space from mixing with biological cells or capture objects in an interior space of another isolation pen of said plurality of isolation pens; and wherein said placing comprises moving the individual biological cell from the micro-fluidic channel into said one of said plurality of isolation pens;

lysing said individual biological cell in said one of said plurality of isolation pens;

capturing with a capture object in said one of said plurality of isolation pens nucleic acid material from said lysed cell; and after said capturing, removing said capture object from said one of said plurality of isolation pens by selectively activating and/or deactivating said DEP electrodes to move said capture object from in said one of said plurality of isolation pens to the micro-fluidic channel.

2. The process of claim 1, wherein said placing further comprises:

selecting said individual biological cell from a group of biological cells in a common space in said micro-fluidic device, and moving said individual biological cell from said common space into said one of said plurality of isolation pens in said micro-fluidic device.

3. The process of claim 2, wherein said selecting comprises testing said group of biological cells in said micro-fluidic device for a particular characteristic.

4. The process of claim 3, wherein said individual biological cell is one of said biological cells in said group that tests positive for said particular characteristic.

5. The process of claim 3, wherein said individual biological cell is one of said biological cells in said group that tests negative for said particular characteristic.

6. The process of claim 3, wherein said particular characteristic comprises a size of said biological cells or a morphology of said biological cells.

7. The process of claim 3, wherein said particular characteristic comprises whether said biological cells comprise a particular material or whether said biological cells produce a particular material.

8. The process of claim 2, wherein said selecting further comprises creating an individual light trap trapping said individual biological cell by projecting a light pattern into said common space inside said micro-fluidic device.

9. The process of claim 8, wherein said moving comprises moving said individual light trap from said common space into said one of said plurality of isolation pens, wherein moving said individual light trap selectively activates and/or deactivates said DEP electrodes at said surface of said substrate.

10. The process of claim 1, wherein a plurality of individual biological cells is placed into a corresponding plurality of isolation pens such that each isolation pen includes a single individual biological cell.

11. The process of claim 10, wherein said lysing comprises lysing said plurality of said individual biological cells in said corresponding plurality of isolation pens simultaneously.

12. The process of claim 10, wherein said lysing step comprises:

selecting a specific individual one of said biological cells in said corresponding plurality of isolation pens, and lysing said specific individual one of said biological cells without also simultaneously lysing any others of said biological cells in said corresponding plurality of isolation pens.

13. The process of claim 10, wherein:

said lysing comprises lysing said plurality of individual biological cells in said corresponding plurality of isolation pens;

said capturing comprises capturing with a plurality of capture objects in said corresponding plurality of isolation pens nucleic acid material from said lysed individual biological cells; and said removing comprises removing said plurality of capture objects from said corresponding plurality of isolation pens.

14. The process of claim 13, wherein:

each of said capture objects comprises an identifier that uniquely identifies each said capture object from every other capture object of said plurality, and said process further comprises storing in a memory device a correlation between each said capture object and data regarding nucleic acid material captured by said capture object.

15. The process of claim 14, wherein said correlation comprises a characteristic of one of said lysed individual biological cells from which said nucleic acid material captured by said capture object originated.

16. The process of claim 1, wherein said lysing comprises:

flowing a lysing reagent through the micro-fluidic channel in said micro-fluidic device to which said one of said plurality of isolation pens is fluidically connected, directing a beam of electromagnetic energy at said individual biological cell, electroporating said individual biological cell, changing a temperature of said individual biological cell sufficiently to lyse said individual biological cell, or applying sufficient acoustic energy to said individual biological cell to lyse said individual biological cell.

17. The process of claim 1, wherein:

said lysing comprises compromising an outer membrane of said individual biological cell without compromising a membrane of a first internal element of said individual biological cell, said compromising said outer membrane releases a first type of nucleic acid from said individual biological cell, and said capture object is a first capture object configured to capture said first type of nucleic acid.

18. The process of claim 17 further comprising repeating said lysing step and said capturing step as follows:

lysing in said one of said plurality of isolation pens said first internal element of said individual biological cell by compromising said membrane of said first internal element, and capturing with a second capture object in said one of said plurality of isolation pens a second type of nucleic acid material released by said lysing said first internal element.

19. The process of claim 18, wherein said first internal element is one of a nucleus or an organelle of said individual biological cell.

20. The process of claim 19, wherein said lysing said individual biological cell further comprises compromising said outer membrane of said first internal element without compromising a membrane of a second internal element of said individual cell.

21. The process of claim 20 further comprising repeating again said lysing and said capturing as follows:

lysing in said one of said plurality of isolation pens said second internal element of said individual biological cell by compromising said membrane of said second internal element, and capturing with a third capture object in said one of said plurality of isolation pens a third type of nucleic acid material released by said lysing said second internal element.

22. The process of claim 21, wherein:

one of said first internal element and said second internal element is a nucleus of said individual biological cell, and the other of said first internal element and said second internal element is an organelle of said individual biological cell.

23. The process of claim 22, wherein:

said first type of nucleic acid material is a different type of nucleic acid material than said second type of nucleic acid material, said second type of nucleic acid material is a different type of nucleic acid material than said third type of nucleic acid material, and said first type of nucleic acid material is a different type of nucleic acid material than said third type of nucleic acid material.

24. The process of claim 1, wherein said individual biological cell is a cell from a clonal cell colony.

25. The process of claim 24, wherein said placing comprises moving said individual biological cell from a clonal cell colony in a culturing pen in said micro-fluidic device into said one of said plurality of isolation pens.

26. The process of claim 25 wherein:

said lysing comprises lysing said individual biological cell in said one of said plurality of isolation pens, said capturing comprises capturing with one or more capture objects in said one of said plurality of isolation pens nucleic acid material from said lysed cell, and said removing comprises removing said one or more capture objects from said one of said plurality of isolation pens.

27. The process of claim 26, wherein:

each of said capture objects comprises an identifier that uniquely identifies each said capture object from every other one of said capture objects, and said process further comprises storing in a memory device a correlation between said identifier of each said capture object and an identification of said clonal cell colony from which said individual cell whose nucleic acid material is captured by said capture object originated.

28. The process of claim 1, wherein said moving the individual biological cell comprises selectively activating and/or deactivating said DEP electrodes at an inner surface of the micro-fluidic channel to move the individual biological cell from the micro-fluidic channel into said one of said plurality of isolation pens.

* * * * *